United States Patent
Matsumoto et al.

(10) Patent No.: US 8,329,687 B2
(45) Date of Patent: Dec. 11, 2012

(54) PYRIDOOXAZEPINE DERIVATIVE AND USE THEREOF

(75) Inventors: Takahiro Matsumoto, Osaka (JP); Tomokazu Kusumoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 254 days.

(21) Appl. No.: 12/742,837

(22) PCT Filed: Nov. 14, 2008

(86) PCT No.: PCT/JP2008/070808
§ 371 (c)(1),
(2), (4) Date: May 13, 2010

(87) PCT Pub. No.: WO2009/063991
PCT Pub. Date: May 22, 2009

(65) Prior Publication Data
US 2010/0286120 A1    Nov. 11, 2010

(30) Foreign Application Priority Data
Nov. 15, 2007  (JP) .................. 2007-297169

(51) Int. Cl.
| A61P 1/00 | (2006.01) |
| A61P 3/04 | (2006.01) |
| A61P 13/00 | (2006.01) |
| A61P 15/00 | (2006.01) |
| A61P 43/00 | (2006.01) |
| A61K 31/553 | (2006.01) |
| C07D 498/04 | (2006.01) |

(52) U.S. Cl. .................. 514/211.1; 540/552
(58) Field of Classification Search ........... 514/211.1; 540/552
See application file for complete search history.

(56) References Cited

U.S. PATENT DOCUMENTS

| 2005/0101591 A1 | 5/2005 | Seto et al. |
| 2009/0131402 A1 | 5/2009 | Shirai et al. |
| 2009/0318412 A1 | 12/2009 | Matsumoto et al. |
| 2010/0173890 A1 | 7/2010 | Nordvall et al. |
| 2011/0053910 A1 | 3/2011 | McKerrecher et al. |

FOREIGN PATENT DOCUMENTS

| EP | 1 489 083 | 12/2004 |
| EP | 1 591 120 | 11/2005 |
| EP | 2 018 863 | 1/2009 |
| EP | 2 123 644 | 11/2009 |
| JP | 2006-56881 | 3/2006 |
| WO | 02/074746 | 9/2002 |
| WO | 2007/004960 | 1/2007 |
| WO | 2007/007040 | 1/2007 |
| WO | 2007/132841 | 11/2007 |
| WO | 2008/007661 | 1/2008 |

OTHER PUBLICATIONS

Supplementary European Search Report issued Sep. 22, 2011 in European Application No. 08849982.7.
International Search Report issued Jan. 13, 2009 in International (PCT) Application No. PCT/JP2008/070808.
English translation of the International Preliminary Report on Patentability and Written Opinion. Jun. 29, 2010.

*Primary Examiner* — Brenda Coleman
(74) *Attorney, Agent, or Firm* — Wenderoth, Lind & Ponack, L.L.P.

(57) ABSTRACT

The present invention provides a compound having a superior serotonin 5-$HT_{2C}$ receptor activating action, which is represented by the formula

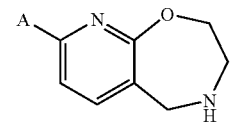

wherein A is $-OR^1$ or $-S(O)_pR^2$, $R^1$ and $R^2$ are the same or different and each is a hydrogen atom, a hydrocarbon group optionally having substituent(s), or a heterocyclic group to optionally having substituent(s), and p is 0, 1 or 2, or a salt thereof.

14 Claims, No Drawings

PYRIDOOXAZEPINE DERIVATIVE AND USE THEREOF

This application is a U.S. national stage of International Application No. PCT/JP2008/070808 filed Nov. 14, 2008.

TECHNICAL FIELD

The present invention relates to a pyridooxazepine derivative having a superior serotonin 5-$HT_{2C}$ receptor activating action and useful as an agent for the treatment or prophylaxis of a lower urinary tract symptom, obesity and/or organ prolapse etc., and the like.

BACKGROUND OF THE INVENTION

Serotonin 5-$HT_{2C}$ receptor is one of the receptors of the biological transmitter serotonin, which is distributed mainly in the central nervous system and controls many physiological functions in vivo. A representative example is the control of appetite. It has been demonstrated in a study using rodents that stimulation of the central serotonin 5-$HT_{2C}$ receptor decreases eating behavior, resulting in decreased body weight. It has also been reported that, in human as well, administration of a serotonin 5-$HT_{2C}$ receptor activator suppresses appetite and decreases body weight (see non-patent document 1). In addition, it has been demonstrated in a at test using a serotonin 5-$HT_{2C}$ receptor activator that stimulation of the central serotonin 5-$HT_{2C}$ receptor suppresses depression-related behaviors (see non-patent document 2), and has also been reported to be effective for many central nervous diseases such as anxiety etc. (see non-patent document 3). The serotonin 5-$HT_{2C}$ receptor is also highly expressed in the parasympathetic nucleus and motorial nerve cell bodies in the sacral spinal cord, and is considered to control the peripheral nervous functions (see non-patent document 4). It has been reported that when a serotonin 5-$HT_{2C}$ receptor activator is administered to rats, penile erection is induced (see non-patent document 5), and urethral resistance is increased (see patent document 1); all these actions are attributed to stimulation of the serotonin 5-$HT_{2C}$ receptor in the sacral spinal cord. For serotonin 5-$HT_{2C}$ receptor activators, many clinical applications are likely, with particular expectations for anti-obesity drugs, anti-depressants, anti-anxiety drugs, therapeutic drugs for male erectile dysfunction, and therapeutic drugs for stress urinary incontinence and the like.

As the pyridooxazepine derivative, the following compounds have been reported.

A compound represented by the formula:

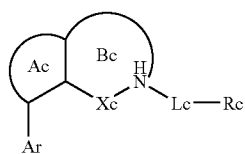

wherein ring Ac is an optionally substituted aromatic ring; ring Bc is a nitrogen-containing 6- to 9-membered ring optionally further having substituent(s) other than -Lc-Rc; Xc is an optionally substituted methylene group; Ar is an optionally substituted aromatic group; Rc is an optionally substituted cyclic group; Lc is an optionally substituted $C_{1-3}$ alkylene group, —CONH—, —$SO_2$NH— or —$SO_2$—, and Xc is not a methylene group substituted by an oxo group (patent document 2);

a compound represented by the formula:

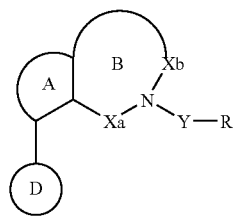

wherein ring A is an optionally further substituted aromatic heterocycle, ring B is an optionally further substituted nitrogen-containing 6- to 9-membered ring, Xa is an optionally substituted methylene group (excluding —C(=O)—), Xb is an optionally substituted methylene group, Y is an optionally substituted $C_{1-3}$ alkylene group, —CONH—, —$SO_2$NH— or —$SO_2$—, R is an optionally substituted aromatic group, and ring D is an optionally substituted aromatic ring or an optionally substituted non-aromatic heterocycle, provided that when ring D is an optionally substituted benzene ring, then the benzene ring has a substituent at the ortho-position relative to the bond with ring A, or Xb is a substituted methylene group (patent document 3);

a compound represented by the formula:

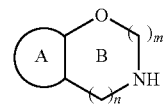

wherein ring A is a 5- or 6-membered aromatic heterocycle optionally having substituent(s), and ring B is a 7- to 9-membered ring optionally having substituent(s) other than an oxo group wherein the combination of m and n (m,n) is (1,2), (2,1), (2,2), (3,1), (3,2) or (4,1) (patent document 4);

a compound represented by the formula:

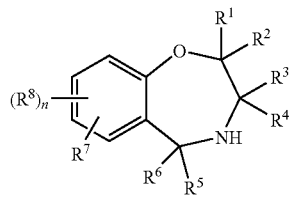

wherein $R^1$, $R^2$, $R^3$, $R^4$, $R^5$ and $R^6$ are the same or different and each is a hydrogen atom and the like; $R^7$ is monoalkylamino group and the like; $R^8$ is a halogen atom and the like; n is an integer of 0 to 3 (patent document 5).

However, none of these documents report the compound of the present invention.

non-patent document 1: Expert Opinion on Investigational Drugs, 2006, vol. 15, p. 257-266
non-patent document 2: J. Pharmacol. Exp. Ther., 1998, vol. 286, p. 913-924
non-patent document 3: Pharmacology Biochemistry Behavior, 2002, vol. 71, p. 533-554
non-patent document 4: Neuroscience, 1999, vol. 92, p. 1523-1537
non-patent document 5: Eur. J. Pharmacol., 2004, vol. 483, p. 37-43 patent document 1: WO2004/096196
patent document 2: WO2004/067008
patent document 3: JP-A-2006-056881
patent document 4: WO2007/132841
patent document 5: WO2008/108445

DISCLOSURE OF THE INVENTION

Problems to be Solved by the Invention

There is a demand on the development of a compound having a serotonin 5-$HT_{2C}$ receptor activating action, which is useful as an agent for the prophylaxis or treatment of lower urinary tract symptom, obesity and/or organ prolapse and the like, and has superior properties in terms of receptor selectivity, efficacy, duration of action, specificity, lower toxicity and the like.

The present invention aims to provide a pyridooxazepine derivative having a serotonin 5-$HT_{2C}$ receptor activating action and the like, which has a chemical structure different from that of known compounds (including the aforementioned compounds), and an agent for the prophylaxis or treatment of diseases such as a lower urinary tract symptom, obesity and/or organ prolapse and the like, containing the pyridooxazepine derivative.

Means of Solving the Problems

The present inventors had conducted intensive studies in an attempt to solve the above-mentioned problems, and found that a compound represented by the following formula

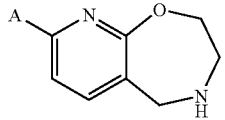

wherein
A is —$OR^1$ or —$S(O)_pR^2$;
$R^1$ and $R^2$ are the same or different and each is
(1) a hydrogen atom,
(2) a hydrocarbon group optionally having substituent(s), or
(3) a heterocyclic group optionally having substituent(s); and
p is 0, 1 or 2,
or a salt thereof (hereinafter sometimes to be referred to as "compound (I)") has a superior serotonin 5-$HT_{2C}$ receptor activating action, and made further studies, which resulted in the completion of the present invention.

Accordingly, the present invention relates to
[1] compound (I),
[2] the compound of the above-mentioned [1], wherein $R^1$ and $R^2$ are the same or different and each is
(1) a hydrogen atom, or
(2) a hydrocarbon group optionally having substituent(s),
[3] the compound of the above-mentioned [1] or [2], wherein the hydrocarbon group optionally having substituent(s) is
(1) an alkyl group optionally having substituent(s),
(2) a cycloalkyl group optionally having substituent(s),
(3) a cycloalkyl-alkyl group optionally having substituent(s),
(4) an aryl group optionally having substituent(s), or
(5) an aralkyl group optionally having substituent(s),
[4] the compound of the above-mentioned [1], wherein p is 0,
[5] the compound of the above-mentioned [1], wherein $R^1$ is
(1) a $C_{1-10}$ alkyl group optionally having 1 to 3 substituents selected from
(i) a halogen atom,
(ii) a mono- or di-$C_{1-6}$ alkylamino group,
(iii) a $C_{1-6}$ alkoxy group or a phenoxy group,
(iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from
(a) a $C_{1-6}$ alkyl group, and
(b) an oxo group,
(v) a thiazolyl group, an imidazolyl group, a pyridyl group, a pyridazinyl group or an indolyl group, each optionally having 1 to 3 substituents selected from
(a) a $C_{1-6}$ alkyl group, and
(b) a piperidinyl group, and
(vi) a sulfamoyl group,
(2) a $C_{7-12}$ aralkyl group optionally having 1 to 3 substituents selected from
(i) a halogen atom, and
(ii) morpholinyl,
(3) a phenyl group optionally having 1 to 3 halogen atoms,
(4) a $C_{3-6}$ cycloalkyl group optionally having 1 to 3 substituents selected from
(i) a halogen atom, and
(ii) a $C_{1-6}$ alkyl group,
(5) a $C_{3-6}$ cycloalkyl-$C_{1-6}$ alkyl group, or
(6) a di-$C_{3-6}$ cycloalkyl-$C_{1-6}$ alkyl group;
$R^2$ is a $C_{1-6}$ alkyl group; and
p is 0,
[6] the compound of the above-mentioned [1], wherein $R^1$ is
(1) a $C_{1-10}$ alkyl group optionally having 1 to 3 substituents selected from
(i) a halogen atom,
(ii) a dimethylamino group or a diethylamino group,
(iii) a methoxy group, an ethoxy group or a phenoxy group,
(iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from
(a) a methyl group, and
(b) an oxo group,
(v) a thiazolyl group, an imidazolyl group, a pyridyl group, a pyridazinyl group or an indolyl group, each optionally having 1 to 3 substituents selected from
(a) a methyl group, and
(b) a piperidinyl group, and
(vi) a sulfamoyl group,
(2) a benzyl group optionally having 1 to 3 substituents selected from
(i) a halogen atom, and
(ii) a morpholinyl group,
(3) a phenyl group optionally having 1 to 3 halogen atoms,
(4) a $C_{3-6}$ cycloalkyl group optionally having 1 to 3 substituents selected from
(i) a halogen atom, and
(ii) a methyl group,
(5) a $C_{3-6}$ cycloalkyl-$C_{1-2}$ alkyl group, or
(6) a di-$C_{3-6}$ cycloalkyl-$C_{1-2}$ alkyl group;
$R^2$ is isopropyl; and
p is 0,
[7] 8-isopropoxy-2,3,4,5-tetrahydropyrido[3,2-f][1,4]oxazepine or a salt thereof,
[8] (−)-8-(1-cyclopropylethoxy)-2,3,4,5-tetrahydropyrido[3,2-f][1,4]oxazepine or a salt thereof,
[9] 8-(2-chlorophenoxy)-2,3,4,5-tetrahydropyrido[3,2-f][1,4]oxazepine or a salt thereof,
[10] 8-{[(1R)-1-methylpropyl]oxy}-2,3,4,5-tetrahydropyrido[3,2-f][1,4]oxazepine or a salt thereof,

[11] 8-(cyclobutyloxy)-2,3,4,5-tetrahydropyrido[3,2-f][1,4]oxazepine or a salt thereof,
[12] 8-(isopropylthio)-2,3,4,5-tetrahydropyrido[3,2-f][1,4]oxazepine or a salt thereof,
[13] a prodrug of compound (I),
[14] a medicament comprising compound (I) or a prodrug thereof,
[15] a medicament of [14], which is a serotonin 5-HT$_{2C}$ receptor activator,
[16] the medicament of [14], which is an agent for the prophylaxis or treatment of a lower urinary tract symptom, obesity and/or organ prolapse,
[17] a method for the prophylaxis or treatment of a lower urinary tract symptom, obesity and/or organ prolapse, comprising administering an effective amount of compound (I) or a prodrug thereof to a mammal,
[18] use of compound (I) or a prodrug thereof for the production of an agent for the prophylaxis or treatment of a lower urinary tract symptom, obesity and/or organ prolapse, and the like.

Effect of the Invention

Since the compound of the present invention has a superior serotonin 5-HT$_{2C}$ receptor activating action, it is useful as a safe drug for the prophylaxis or treatment of all serotonin 5-HT$_{2C}$-associated diseases, for example, lower urinary tract symptom, obesity and/or organ prolapse and the like.

DETAILED DESCRIPTION OF THE INVENTION

The present invention is explained in detail in the following.

In the present specification, examples of the "halogen atom" include a fluorine atom, a chlorine atom, a bromine atom and an iodine atom.

In the present specification, examples of the "alkyl group" include a linear or branched chain alkyl group and, for example, a $C_{1-10}$ alkyl group (e.g., methyl, ethyl, propyl, isopropyl, butyl, isobutyl, sec-butyl, tert-butyl, 1-methylpropyl, pentyl, isopentyl, 1,2-dimethylpropyl, hexyl, 2-methylpentyl, 3-methylpentyl, 1,2-dimethylbutyl, 1,2,2-trimethylpropyl, heptyl, 3-methylhexyl, octyl, 1-isopropyl-3-methylbutyl, 3-methyl-1-(1-methylethyl)butyl, 2-ethylhexyl, decyl and 4-propylpentyl).

In the present specification, examples of the "$C_{1-6}$ alkyl group" include methyl, ethyl, propyl, isopropyl, butyl, isobutyl, sec-butyl, tert-butyl, 1-methylpropyl, pentyl, isopentyl, 1,2-dimethylpropyl, hexyl, 2-methylpentyl, 3-methylpentyl, 1,2-dimethylbutyl and 1,2,2-trimethylpropyl.

In the present specification, examples of the "$C_{1-6}$ alkoxy group" include methoxy, ethoxy, propoxy, isopropoxy, butoxy, isobutoxy, sec-butoxy, tert-butoxy, pentoxy, isopentoxy and hexoxy.

In the present specification, examples of the "cycloalkyl group" include a $C_{3-6}$ cycloalkyl group (e.g., cyclopropyl, cyclobutyl, cyclopentyl and cyclohexyl).

In the present specification, examples of the "cycloalkyl-alkyl group" include a cycloalkyl-alkyl group (e.g., cyclopropylmethyl, cyclopropylethyl, cyclobutylmethyl, cyclobutylethyl), wherein the alkyl moiety is the above-mentioned "alkyl group" and the cycloalkyl moiety is the above-mentioned "cycloalkyl group".

In the present specification, examples of the "aryl group" include a $C_{6-12}$ aryl group (e.g., phenyl, naphthyl).

In the present specification, examples of the "aralkyl group" include a $C_{7-12}$ aralkyl group (e.g., benzyl, 2-phenylethyl, 1-phenylethyl, 3-phenylpropyl).

In the present specification, examples of the "heterocyclic group" include a 5- to 14-membered aromatic heterocyclic group and a 5- to 14-membered nonaromatic heterocyclic group. Specific examples include
(1) a 5- to 8-membered monocyclic nonaromatic heterocyclic group containing, besides carbon atom, 1 to 4 hetero atoms selected from nitrogen atom, sulfur atom and oxygen atom (e.g., pyrrolidinyl, tetrahydrofuryl, tetrahydrothienyl, piperidinyl, tetrahydropyranyl, morpholinyl, thiomorpholinyl, piperazinyl, azepanyl, 1,4-diazepanyl, oxazepanyl (e.g., 1,4-oxazepanyl));
(2) a 5- to 8-membered monocyclic aromatic heterocyclic group containing, besides carbon atom, 1 to 4 hetero atoms selected from nitrogen atom, sulfur atom and oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl);
(3) a 8- to 14-membered condensed nonaromatic heterocyclic group induced from a ring wherein a ring corresponding to the above-mentioned "5- to 8-membered nonaromatic heterocyclic group" is condensed with 5- or 6-membered aromatic heterocycle (e.g., thiophene, pyrrole, imidazole, pyrazole, pyrazine), $C_{3-8}$ cycloalkane (e.g., cyclopropane, cyclobutane, cyclopentane, cyclohexane, cycloheptane, cyclooctane), or $C_{6-12}$ arene (e.g., benzene, naphthalene) (e.g., dihydroindolyl, dihydroisoindolyl, dihydrobenzofuranyl, tetrahydrobenzofuranyl, dihydrobenzodioxinyl, dihydrobenzodioxepinyl, chromenyl, dihydrochromenyl, dihydroquinolinyl, tetrahydroquinolinyl, dihydroisoquinolinyl, tetrahydroisoquinolinyl, dihydrophthalazinyl, benzotriazolyl, dihydrobenzooxazinyl (e.g., 3,4-dihydro-2H-benzo[1,4]oxazinyl));
(4) a 8- to 14-membered condensed aromatic heterocyclic group induced from a ring wherein a ring corresponding to the above-mentioned "5- to 8-membered aromatic heterocyclic group" is condensed with 5- or 6-membered aromatic heterocycle (e.g., thiophene, pyrrole, imidazole, pyrazole, pyrazine), $C_{3-8}$ cycloalkane (e.g., cyclopropane, cyclobutane, cyclopentane, cyclohexane, cycloheptane, cyclooctane), or $C_{6-12}$ arene (e.g., benzene, naphthalene) (e.g., quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, pyrrolopyrazinyl, imidazopyridinyl, thienopyridinyl, imidazopyrazinyl, pyrazolopyridinyl, pyrazolothienyl, pyrazolotriazinyl); and the like.

The above-mentioned heterocyclic group may be oxidized. For example, when the heterocyclic group contains a nitrogen atom and/or a sulfur atom, the nitrogen atom and/or the sulfur atom may be oxidized.

Furthermore, the above-mentioned heterocyclic group may form a Spiro bond with $C_{3-8}$ cycloalkane (e.g., cyclopropane, cyclobutane, cyclopentane, cyclohexane, cycloheptane, cyclooctane), condensed cycloalkane (e.g., indane) or the like.

In the present specification, examples of the "hydrocarbon group optionally having substituent(s)" include "alkyl group optionally having substituent(s)", "alkenyl group optionally having substituent(s)", "alkynyl group optionally having substituent(s)", "aralkyl group optionally having substituent(s)", "aryl group optionally having substituent(s)", "cycloalkyl group optionally having substituent(s)", "cycloalkyl-alkyl group optionally having substituent(s)" and the like.

Examples of the substituent that the alkyl group of the "alkyl group optionally having substituent(s)" optionally has include those selected from
(1) a halogen atom,
(2) a cyano group,
(3) a hydroxy group,
(4) a nitro group,
(5) a formyl group,
(6) an amino group,
(7) a mono- or di-$C_{1-6}$ alkylamino group (e.g., methylamino, ethylamino, propylamino, dimethylamino, diethylamino, dipropylamino),
(8) a $C_{1-6}$ alkyl-carbonylamino group (e.g., acetylamino, ethylcarbonylamino),
(9) a $C_{1-6}$ alkoxy-carbonylamino group (e.g., methoxycarbonylamino, ethoxycarbonylamino, propoxycarbonylamino),
(10) a $C_{1-6}$ alkoxy group optionally substituted by halogen atom(s),
(11) a $C_{7-12}$ aralkyloxy group (e.g., benzyloxy),
(12) a $C_{6-12}$ aryloxy group (e.g., phenoxy),
(13) a carboxyl group,
(14) a $C_{1-6}$ alkoxy-carbonyl group (e.g., methoxycarbonyl, ethoxycarbonyl, propoxycarbonyl, isopropoxycarbonyl, tert-butoxycarbonyl),
(15) a $C_{7-12}$ aralkyloxy-carbonyl group (e.g., benzyloxycarbonyl),
(16) a $C_{6-12}$ aryloxy-carbonyl group (e.g., phenyloxycarbonyl),
(17) a $C_{1-6}$ alkyl-carbonyl group (e.g., acetyl, ethylcarbonyl, propylcarbonyl, isopropylcarbonyl, 2,2-dimethylpropylcarbonyl),
(18) a $C_{3-8}$ cycloalkyl-carbonyl group (e.g., cyclopropylcarbonyl, cyclobutylcarbonyl, cyclopentylcarbonyl, cyclohexylcarbonyl),
(19) a $C_{7-12}$ aralkyl-carbonyl group (e.g., benzylcarbonyl),
(20) a carbamoyl group,
(21) a thiocarbamoyl group,
(22) a mono- or di-$C_{1-6}$ alkyl-carbamoyl group (e.g., methylcarbamoyl, ethylcarbamoyl, propylcarbamoyl, isopropylcarbamoyl, dimethylcarbamoyl, diethylcarbamoyl, dipropylcarbamoyl),
(23) a mono- or di-$C_{7-12}$ aralkyl-carbamoyl group (e.g., benzylcarbamoyl, dibenzylcarbamoyl),
(24) a thiol group,
(25) a $C_{1-6}$ alkylthio group (e.g., methylthio, ethylthio, propylthio),
(26) a $C_{7-12}$ aralkylthio group (e.g., benzylthio),
(27) a $C_{1-6}$ alkylsulfonyl group (e.g., methylsulfonyl, ethylsulfonyl, propylsulfonyl, isopropylsulfonyl),
(28) a $C_{3-8}$ cycloalkylsulfonyl group (e.g., cyclopropylsulfonyl, cyclobutylsulfonyl, cyclopentylsulfonyl),
(29) a $C_{6-12}$ arylsulfonyl group (e.g., phenylsulfonyl, 1-naphthylsulfonyl, 2-naphthylsulfonyl),
(30) a $C_{7-12}$ aralkylsulfonyl group (e.g., benzylsulfonyl),
(31) a 5- to 14-membered nonaromatic heterocyclic group containing, besides carbon atom, 1 to 4 hetero atoms selected from nitrogen atom, sulfur atom and oxygen atom (e.g., pyrrolidinyl, tetrahydrofuryl, tetrahydrothienyl, piperidinyl, tetrahydropyranyl, morpholinyl, thiomorpholinyl, piperazinyl, azepanyl, oxazepanyl, benzotriazolyl, 3,4-dihydro-2H-benzo[1,4]oxazinyl) optionally having 1 to 3 substituents selected from
(i) a halogen atom,
(ii) a $C_{1-6}$ alkyl group,
(iii) a $C_{1-6}$ alkoxy group,
(iv) a $C_{6-12}$ arylsulfonyl group (e.g., phenylsulfonyl),
(v) an oxo group, and
(vi) a heterocyclic group (e.g., morpholinyl, pyridyl, piperidinyl, pyrrolidinyl, imidazopyridyl, benzimidazolyl),
(32) a 5- to 14-membered aromatic heterocyclic group containing, besides carbon atom, 1 to 4 hetero atoms selected from nitrogen atom, sulfur atom and oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, imidazopyridyl, indolyl) optionally having 1 to 3 substituents selected from
(i) a halogen atom,
(ii) a $C_{1-6}$ alkyl group,
(iii) a $C_{1-6}$ alkoxy group,
(iv) a $C_{6-12}$ arylsulfonyl group (e.g., phenylsulfonyl),
(v) an oxo group, and
(vi) a heterocyclic group (e.g., morpholinyl, pyridyl, piperidinyl, pyrrolidinyl, imidazopyridyl, benzimidazolyl),
(33) a 5- to 8-membered non-aromatic heterocyclyl-carbonyl group containing, besides carbon atom, 1 to 4 hetero atoms selected from nitrogen atom, sulfur atom and oxygen atom (e.g., pyrrolidinylcarbonyl, tetrahydrofurylcarbonyl, tetrahydrothienylcarbonyl, piperidinylcarbonyl, tetrahydropyranylcarbonyl, morpholinylcarbonyl, thiomorpholinylcarbonyl, piperazinylcarbonyl),
(34) a 5- to 8-membered aromatic heterocyclyl-carbonyl group containing, besides carbon atom, 1 to 4 hetero atoms selected from nitrogen atom, sulfur atom and oxygen atom (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyrazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, 1,2,3-triazolylcarbonyl, 1,2,4-triazolylcarbonyl, tetrazolylcarbonyl, pyridylcarbonyl, pyridazinylcarbonyl, pyrimidinylcarbonyl, pyrazinylcarbonyl, triazinylcarbonyl),
(35) a ureido group,
(36) a $C_{1-6}$ alkylureido group (e.g., methylureido, ethylureido, propylureido),
(37) a $C_{6-12}$ arylureido group (e.g., phenylureido, 1-naphthylureido, 2-naphthylureido),
(38) a $C_{1-4}$ alkylenedioxy group (e.g., methylenedioxy, ethylenedioxy, propylenedioxy),
(39) a sulfamoyl group
and the like, wherein the number of the substituents is 1 to 4, preferably 1 to 3.

Examples of the "alkenyl group optionally having substituent(s)" include a $C_{2-6}$ alkenyl group (e.g., vinyl, 1-propenyl, allyl, isopropenyl, butenyl, isobutenyl) optionally having 1 to 4, preferably 1 to 3, substituents optionally possessed by the alkyl group of the above-mentioned "alkyl group optionally having substituent(s)" and the like.

Examples of the "alkynyl group optionally having substituent(s)" include a $C_{2-6}$ alkynyl group (e.g., ethynyl, propargyl, butynyl, 1-hexynyl) optionally having 1 to 4, preferably 1 to 3, substituents optionally possessed by the alkyl group of the above-mentioned "alkyl group optionally having substituent(s)" and the like.

Examples of the "aralkyl group optionally having substituent(s)" include (1) a substituent which the alkyl group of the above-mentioned "alkyl group optionally having substituent(s)" optionally has, and
(2) a $C_{7-12}$ aralkyl group (e.g., benzyl, 2-phenylethyl, 1-phenylethyl, 3-phenylpropyl) optionally having 1 to 4 substituents (preferably 1 to 3 substituents) selected from
    (i) a $C_{1-6}$ alkyl group optionally having 1 to 3 substituents selected from
        (a) a halogen atom,
        (b) a $C_{1-6}$ alkyl group,
        (c) a $C_{1-6}$ alkoxy group,
        (d) a $C_{6-12}$ arylsulfonyl group (e.g., phenylsulfonyl), and
        (e) a heterocyclic group (e.g., morpholinyl, pyridyl, imidazopyridyl, benzimidazolyl),
    (ii) a $C_{7-12}$ aralkyl group (e.g., benzyl, 2-phenylethyl, 1-phenylethyl, 3-phenylpropyl, 4-phenylbutyl),
    (iii) a $C_{3-8}$ cycloalkyl group (e.g., cyclopropyl, cyclobutyl, cyclopentyl, cyclohexyl), and
    (iv) a $C_{6-12}$ aryl group (e.g., phenyl, 1-naphthyl, 2-naphthyl) optionally having 1 to 3 substituents selected from
        (a) a halogen atom,
        (b) a $C_{1-6}$ alkyl group,
        (c) a $C_{1-6}$ alkoxy group, and
        (d) a heterocyclic group (e.g., morpholinyl, pyridyl, piperidinyl, imidazopyridyl, benzimidazolyl).

Examples of the "aryl group optionally having substituent(s)" include a $C_{6-12}$ aryl group (e.g., phenyl, naphthyl) optionally having 1 to 4, preferably 1 to 3, substituents optionally possessed by the above-mentioned "aralkyl group optionally having substituent(s)".

Examples of the "cycloalkyl group optionally having substituent(s)" include a $C_{3-6}$ cycloalkyl group (e.g., cyclopropyl, cyclobutyl, cyclopentyl, cyclohexyl) optionally having 1 to 4, preferably 1 to 3, substituents optionally possessed by the above-mentioned "aralkyl group optionally having substituent(s)".

Examples of the "cycloalkyl-alkyl group optionally having substituent(s)" include a $C_{3-6}$ cycloalkyl-$C_{1-6}$ alkyl group (e.g., cyclopropylmethyl, dicyclopropylmethyl, 1-cyclopropylethyl, 2-cyclopropylethyl, cyclobutylmethyl, 1-cyclobutylethyl, 2-cyclobutylethyl, cyclopentylmethyl, 1-cyclopentylethyl, 2-cyclopentylethyl, cyclohexylmethyl, 1-cyclohexylethyl, 2-cyclohexylethyl) optionally having, at the cycloalkyl moiety, 1 to 4 substituents (preferably 1 to 3 substituents) that the above-mentioned "aralkyl group optionally having substituent(s)" optionally has.

In the present specification, examples of the "heterocyclic group optionally having substituent(s)" include (1) a 5- to 14-membered nonaromatic heterocyclic group (preferably a 5- to 8-membered monocyclic nonaromatic heterocyclic group) (e.g., pyrrolidinyl, tetrahydrofuryl, tetrahydrothienyl, piperidinyl, tetrahydropyranyl, morpholinyl, thiomorpholinyl, piperazinyl, azepanyl, 1,4-diazepanyl, oxazepanyl (e.g., 1,4-oxazepanyl)) optionally having 1 to 3 substituents that the aralkyl group of the above-mentioned "aralkyl group optionally having substituent(s)" optionally has;
(2) a 5- to 14-membered aromatic heterocyclic group (preferably a 5- to 8-membered monocyclic aromatic heterocyclic group) (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl) optionally having 1 to 3 substituents selected from the substituents that the aralkyl group of the above-mentioned "aralkyl group optionally having substituent(s)" optionally has and an oxo group; and the like.

The present invention provides compound (I) or a prodrug thereof.

In compound (I),
A is a group represented by —$OR^1$ or a group represented by —$S(O)_pR^2$.
$R^1$ and $R^2$ are the same or different and each is
(1) a hydrogen atom,
(2) a hydrocarbon group optionally having substituent(s), or
(3) a heterocyclic group optionally having substituent(s).
$R^1$ and $R^2$ are preferably the same or different and each is
(1) a hydrogen atom, or
(2) a hydrocarbon group optionally having substituent(s).

In addition, the "hydrocarbon group optionally having substituent(s)" shown by $R^1$ or $R^2$ is preferably an alkyl group optionally having substituent(s), a cycloalkyl group optionally having substituent(s), a cycloalkyl-alkyl group optionally having substituent(s), an aryl group optionally having substituent(s) or an aralkyl group optionally having substituent(s).

p is 0, 1 or 2, preferably 0.

$R^1$ is preferably
(1) a $C_{1-10}$ alkyl group optionally having 1 to 3 substituents selected from
    (i) a halogen atom,
    (ii) an amino group,
    (iii) a mono- or di-$C_{1-6}$ alkylamino group (e.g., methylamino, ethylamino, propylamino, dimethylamino, diethylamino, dipropylamino),
    (iv) a $C_{1-6}$ alkoxy group optionally substituted by 1 to 3 halogen atoms,
    (v) a $C_{6-12}$ aryloxy group (e.g., phenoxy etc.),
    (vi) a 5- to 14-membered nonaromatic heterocyclic group containing, besides carbon atom, 1 to 4 hetero atoms selected from nitrogen atom, sulfur atom and oxygen atom (e.g., pyrrolidinyl, tetrahydrofuryl, tetrahydrothienyl, piperidinyl, tetrahydropyranyl, morpholinyl, thiomorpholinyl, piperazinyl, azepanyl, oxazepanyl, benzotriazolyl, 3,4-dihydro-2H-benzo[1,4]oxazinyl) optionally having 1 to 3 substituents selected from
        (a) a halogen atom,
        (b) a $C_{1-6}$ alkyl group,
        (c) a $C_{1-6}$ alkoxy group,
        (d) a $C_{6-12}$ arylsulfonyl group (e.g., phenylsulfonyl),
        (e) an oxo group, and
        (f) a heterocyclic group (e.g., morpholinyl, pyridyl, piperidinyl, pyrrolidinyl, imidazopyridyl, benzimidazolyl),
    (vii) a 5- to 14-membered aromatic heterocyclic group containing, besides carbon atom, 1 to 4 hetero atoms selected from nitrogen atom, sulfur atom and oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, imidazopyridyl, indolyl) optionally having 1 to 3 substituents selected from
        (a) a halogen atom,
        (b) a $C_{1-6}$ alkyl group,
        (c) a $C_{1-6}$ alkoxy group,
        (d) a $C_{6-12}$ arylsulfonyl group (e.g., phenylsulfonyl),
        (e) an oxo group, and (f) a heterocyclic group (e.g., morpholinyl, pyridyl, piperidinyl, pyrrolidinyl, imidazopyridyl, benzimidazolyl), and
(viii) a sulfamoyl group,
(2) a $C_{7-12}$ aralkyl group (e.g., benzyl group) optionally having 1 to 3 substituents selected from
  (i) a halogen atom,
  (ii) a 5- to 14-membered nonaromatic heterocyclic group containing, besides carbon atom, 1 to 4 hetero atoms selected from nitrogen atom, sulfur atom and oxygen atom (e.g., pyrrolidinyl, tetrahydrofuryl, tetrahydrothienyl, piperidinyl, tetrahydropyranyl, morpholinyl, thiomorpholinyl, piperazinyl, azepanyl, oxazepanyl, benzotriazolyl, 3,4-dihydro-2H-benzo[1,4]oxazinyl) optionally having 1 to 3 substituents selected from
    (a) a halogen atom,
    (b) a $C_{1-6}$ alkyl group,
    (c) a $C_{1-6}$ alkoxy group,
    (d) a $C_{6-12}$ arylsulfonyl group (e.g., phenylsulfonyl),
    (e) an oxo group, and
    (f) a heterocyclic group (e.g., morpholinyl, pyridyl, piperidinyl, pyrrolidinyl, imidazopyridyl, benzimidazolyl), and
  (iii) a 5- to 14-membered aromatic heterocyclic group containing, besides carbon atom, 1 to 4 hetero atoms selected from nitrogen atom, sulfur atom and oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, imidazopyridyl, indolyl) optionally having 1 to 3 substituents selected from
    (a) a halogen atom,
    (b) a $C_{1-6}$ alkyl group,
    (c) a $C_{1-6}$ alkoxy group,
    (d) a $C_{6-12}$ arylsulfonyl group (e.g., phenylsulfonyl),
    (e) an oxo group, and
    (f) a heterocyclic group (e.g., morpholinyl, pyridyl, piperidinyl, pyrrolidinyl, imidazopyridyl, benzimidazolyl),
(3) a $C_{6-12}$ aryl group (e.g., phenyl) optionally having 1-3 halogen atoms,
(4) a $C_{3-6}$ cycloalkyl group optionally having 1 to 3 substituents selected from
  (i) a halogen atom, and
  (ii) a $C_{1-6}$ alkyl group optionally substituted by 1 to 3 substituents selected from
    (a) a halogen atom,
    (b) a $C_{1-6}$ alkyl group,
    (c) a $C_{1-6}$ alkoxy group,
    (d) a $C_{6-12}$ arylsulfonyl group, and
    (e) a heterocyclic group,
(5) a $C_{3-6}$ cycloalkyl-$C_{1-6}$ alkyl group, or
(6) a di-$C_{3-6}$ cycloalkyl-$C_{1-6}$ alkyl group (e.g., dicyclopropylmethyl group).
$R^1$ is more preferably
(1) a $C_{1-10}$ alkyl group optionally having 1 to 3 substituents selected from
  (i) a halogen atom,
  (ii) a mono- or di-$C_{1-6}$ alkylamino group,
  (iii) a $C_{1-6}$ alkoxy group or a phenoxy group,
  (iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from a $C_{1-6}$ alkyl group and an oxo group,
  (v) a thiazolyl group, an imidazolyl group, a pyridyl group, a pyridazinyl group or an indolyl group, each optionally having 1 to 3 substituents selected from a $C_{1-6}$ alkyl group and a piperidinyl group, and
  (vi) a sulfamoyl group,
(2) a $C_{7-12}$ aralkyl group optionally having 1 to 3 substituents selected from a halogen atom and a morpholinyl group,
(3) a phenyl group optionally having 1-3 halogen atoms,
(4) a $C_{3-6}$ cycloalkyl group optionally having 1 to 3 substituents selected from a halogen atom and a $C_{1-6}$ alkyl group,
(5) a $C_{3-6}$ cycloalkyl-$C_{1-6}$ alkyl group, or
(6) a di-$C_{3-6}$ cycloalkyl-$C_{1-6}$ alkyl group.
$R^1$ is more preferably
(1) a $C_{1-10}$ alkyl group optionally having 1 to 3 substituents selected from
  (i) a halogen atom (e.g., fluorine atom, chlorine atom),
  (ii) a dimethylamino group or a diethylamino group,
  (iii) a methoxy group, an ethoxy group or a phenoxy group,
  (iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from a methyl group and an oxo group,
  (v) a thiazolyl group, an imidazolyl group, a pyridyl group, a pyridazinyl group or an indolyl group, each optionally having 1 to 3 substituents selected from a methyl group and a piperidinyl group, and
  (vi) a sulfamoyl group,
(2) a benzyl group optionally having 1 to 3 substituents selected from a halogen atom (e.g., fluorine atom, chlorine atom) and a morpholinyl group,
(3) a phenyl group optionally having 1-3 halogen atoms (e.g., fluorine atom, chlorine atom),
(4) a $C_{3-6}$ cycloalkyl group optionally having 1 to 3 substituents selected from a halogen atom (e.g., fluorine atom, chlorine atom) and a methyl group,
(5) a $C_{3-6}$ cycloalkyl-$C_{1-2}$ alkyl group, or
(6) a di-$C_{3-6}$ cycloalkyl-$C_{1-2}$ alkyl group (e.g., dicyclopropylmethyl).
As $R^2$, a group similar to the above-mentioned preferable embodiment of $R^1$ is preferable, and a $C_{1-10}$ alkyl group (e.g., isopropyl) is particularly preferable.
As A, —$OR^1$ or —$SR^2$ (i.e., p=0) is preferable, and —$OR^1$ is particularly preferable.
As compound (I), the compounds described in Examples 1-62 and the like are preferable.
Other preferable examples of compound (I) include the following compounds.
[Compound A]
  Compound (I) wherein
  A is —$OR^1$ or —$SR^2$, and
  $R^1$ and $R^2$ are the same or different and each is
  (1) a hydrogen atom, or
  (2) a hydrocarbon group optionally having substituent(s) (e.g., alkyl group, cycloalkyl group, cycloalkyl-alkyl group, aryl group or aralkyl group).
[Compound B]
  Compound (I) wherein
  A is —$OR^1$ or —$SR^2$,
  $R^1$ is
  (1) a $C_{1-10}$ alkyl group optionally having 1 to 3 substituents selected from
    (i) a halogen atom,
    (ii) a mono- or di-$C_{1-6}$ alkylamino group, (iii) a $C_{1-6}$ alkoxy group or a phenoxy group,
(iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from a $C_{1-6}$ alkyl group and an oxo group,
(v) a thiazolyl group, an imidazolyl group, a pyridyl group, a pyridazinyl group or an indolyl group, each optionally having 1 to 3 substituents selected from a $C_{1-6}$ alkyl group and a piperidinyl group, and
(vi) a sulfamoyl group,
(2) a $C_{7-12}$ aralkyl group optionally having 1 to 3 substituents selected from a halogen atom and a morpholinyl group,
(3) a phenyl group optionally having 1-3 halogen atoms,
(4) a $C_{3-6}$ cycloalkyl group optionally having 1 to 3 substituents selected from a halogen atom and a $C_{1-6}$ alkyl group,
(5) a $C_{3-6}$ cycloalkyl-$C_{1-6}$ alkyl group, or
(6) a di-$C_{3-6}$ cycloalkyl-$C_{1-6}$ alkyl group; and
$R^2$ is a $C_{1-6}$ alkyl group.
[Compound C]
Compound (I) wherein
A is —$OR^1$ or —$SR^2$,
$R^1$ is
(1) a $C_{1-10}$ alkyl group optionally having 1 to 3 substituents selected from
(i) a halogen atom (e.g., fluorine atom, chlorine atom),
(ii) a dimethylamino group or a diethylamino group,
(iii) a methoxy group, an ethoxy group or a phenoxy group,
(iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from a methyl group and an oxo group,
(v) a thiazolyl group, an imidazolyl group, a pyridyl group, a pyridazinyl group or an indolyl group, each optionally having 1 to 3 substituents selected from a methyl group and a piperidinyl group, and
(vi) a sulfamoyl group,
(2) a benzyl group optionally having 1 to 3 substituents selected from a halogen atom (e.g., fluorine atom, chlorine atom) and a morpholinyl group,
(3) a phenyl group optionally having 1-3 halogen atoms (e.g., fluorine atom, chlorine atom),
(4) a $C_{3-6}$ cycloalkyl group optionally having 1 to 3 substituents selected from a halogen atom (e.g., fluorine atom, chlorine atom) and a methyl group,
(5) a $C_{3-6}$ cycloalkyl-$C_{1-2}$ alkyl group, or
(6) a di-$C_{3-6}$ cycloalkyl-$C_{1-2}$ alkyl group (e.g., dicyclopropylmethyl); and
$R^2$ is isopropyl.
[Compound D]
The above-mentioned compound A, compound B or compound C, wherein A is —$OR^1$.
[Compound E]
The following compounds or a salt thereof:
8-isopropoxy-2,3,4,5-tetrahydropyrido[3,2-f][1,4]oxazepine or a salt thereof (Examples 4 and 5);
(−)-8-(1-cyclopropylethoxy)-2,3,4,5-tetrahydropyrido[3,2-f][1,4]oxazepine or a salt thereof (Example 35);
8-(2-chlorophenoxy)-2,3,4,5-tetrahydropyrido[3,2-f][1,4]oxazepine or a salt thereof (Example 32);
8-{[(1R)-1-methylpropyl]oxy}-2,3,4,5-tetrahydropyrido[3,2-f][1,4]oxazepine or a salt thereof (Example 27);
8-(cyclobutyloxy)-2,3,4,5-tetrahydropyrido[3,2-f][1,4]oxazepine or a salt thereof (Example 8);
8-(isopropylthio)-2,3,4,5-tetrahydropyrido[3,2-f][1,4]oxazepine or a salt thereof (Example 37).

When compound (I) is a salt, examples of the salt include salt with inorganic base, ammonium salt, salt with organic to base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound (I) encompasses solvates, for example, hydrates. Alternatively, compound (I) may be a non-solvate (including non-hydrate). In addition, compound (I) may be labeled with an isotope (e.g., $^3H$, $^{14}C$, $^{35}S$, $^{125}I$ and the like) and the like. Compound (I) may also be a deuterium converter wherein $^1H$ is converted to $^2H(D)$.

When compound (I) of the present invention have an asymmetric center, isomers such as enantiomer, diastereomer and the like may be present. Such isomers and a mixture thereof are all encompassed in the scope of the present invention. When an isomer due to conformation is present, such isomer and a mixture thereof are also encompassed in compound (I).

The production methods of the compounds of the present invention are explained in the following.

Compound (I) and a starting compound therefor can be produced by a method known per se, for example, a method shown in the following scheme and the like. In the following, the "room temperature" generally shows 10 to 30° C., and each symbol in the chemical structures described in the scheme is as defined above unless otherwise specified. The compound in the formula also contains salts, and examples of such salts include those similar to the salt of compound (I) and the like.

In addition, in each of the following reactions, when the starting compounds and intermediates have an amino group, a carboxyl group or a hydroxyl group as a substituent, these groups may be protected by a protecting group generally used in the peptide chemistry and the like. In this case, the object compound can be obtained by removing the protecting group as necessary after the reaction.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-12}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups may be substituted by 1 to 3 substituents selected from a halogen atom, a $C_{1-6}$ alkoxy group and a nitro group.

Examples of the carboxyl-protecting group include a $C_{1-6}$ alkyl group, a $C_{7-12}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxyl-protecting group include a $C_{1-6}$ alkyl group, a phenyl group, a trityl group, a $C_{7-12}$ aralkyl group (e.g., benzyl), a formyl group, a $C_{1-6}$ alkyl-carbonyl group, a benzoyl group, a $C_{7-12}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

These groups may be substituted by 1 to 3 substituents selected from a halogen atom, a $C_{1-6}$ alkyl group, a $C_{1-6}$ alkoxy group and a nitro group.

Examples of the method for the removal of the above-mentioned protecting group include a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide and the like) and the like, a reduction method and the like can be used.

In addition, while the compound obtained in each step can be used for the next reaction as a reaction mixture or a crude product, it can also be isolated from a reaction mixture according to a conventional method, or can be easily purified by a separation means such as recrystallization, distillation, chromatography and the like.

Compound (I) can be produced by, for example, the following method A, method B, method C, method D, method E or method F. A starting compound for each method may be a commercially available product or can be produced from the corresponding compound according to a method known per se to those of ordinary skill in the art. In addition, the final products (compounds (Ia) to (If)) of each method are all encompassed in compound (I).

Method A

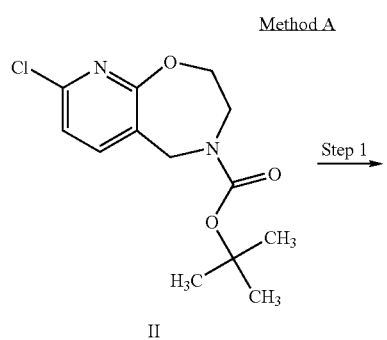

II

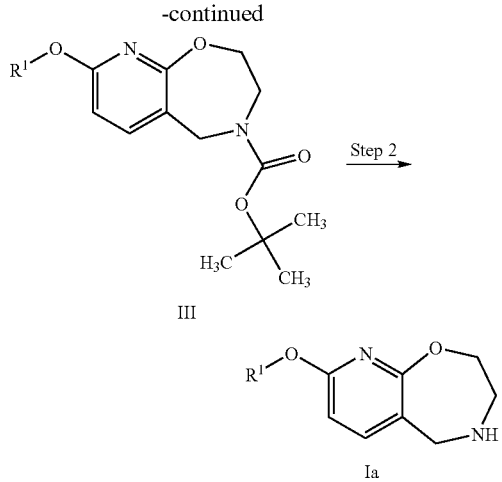

III

Ia

Method B

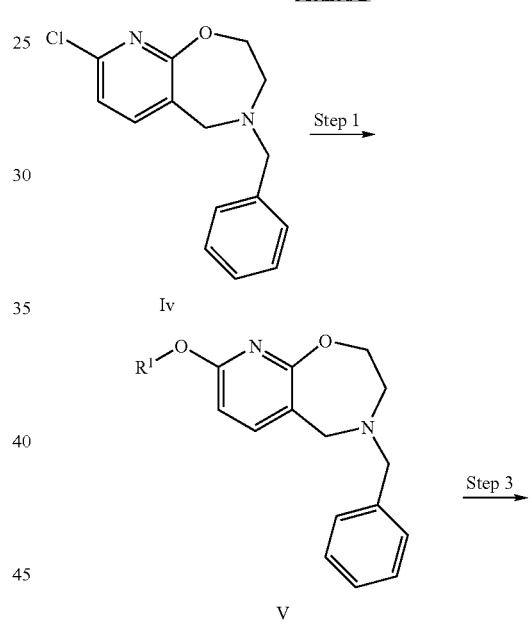

Iv

V

Ib

Method C

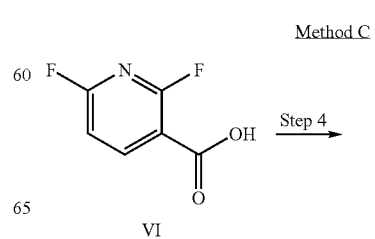

VI

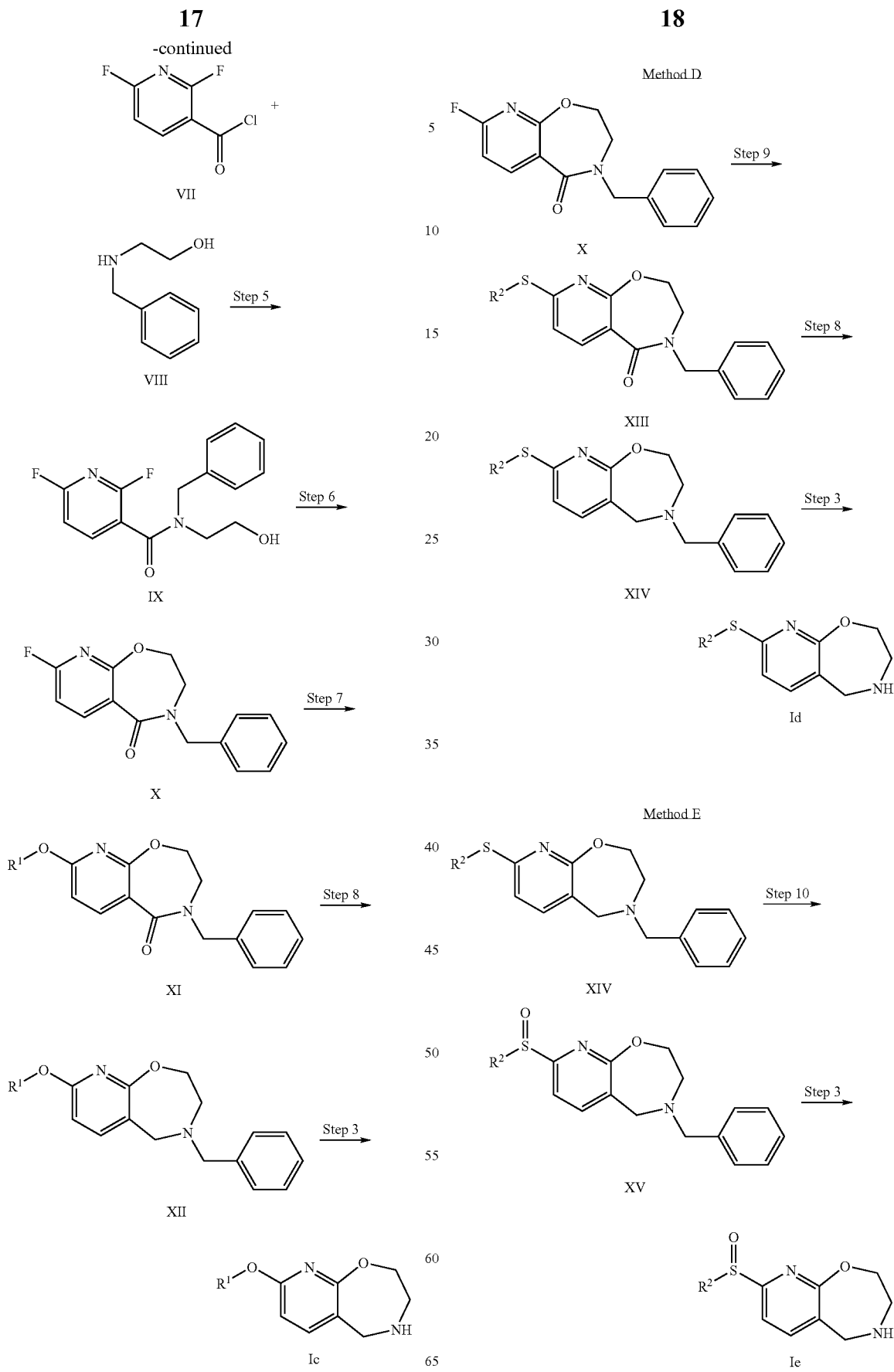

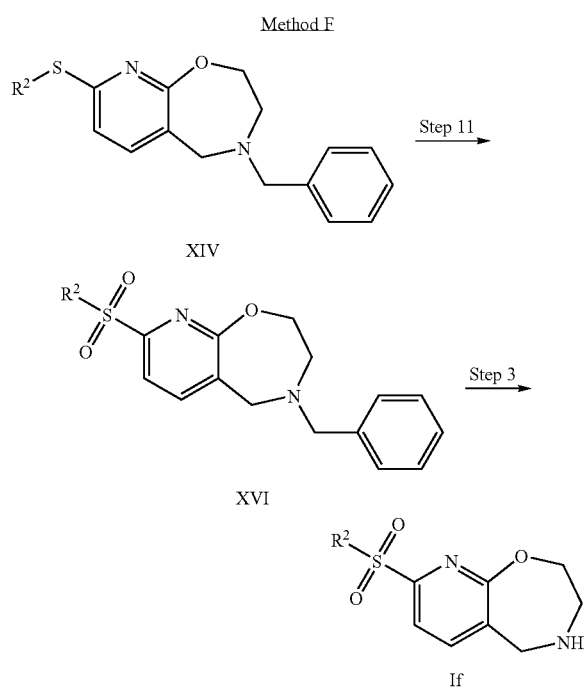

(Method A)
(Step 1)

In this step, a compound represented by the formula (II) or a salt thereof (hereinafter to be referred to as compound (II)) is reacted with alcohol represented by the formula: $R^1$—OH wherein each symbol is as defined above, or a salt thereof, subjected to an alkoxylation reaction, and converted to a compound represented by the formula (III) or a salt thereof (hereinafter to be referred to as compound (III)). Compound (II) can be produced from a corresponding compound by a method known per se to those of ordinary skill in the art.

This step can be performed according to a method known per se [e.g., J. Am. Soc. Chem. 1997, vol. 119, page 3395 and the like], for example, in the presence of a transition metal catalyst and a base in a solvent that does not adversely influence the reaction.

The amount of alcohol or a salt thereof to be used is generally about 1 molar equivalent to about 100 molar equivalents, preferably about 1 molar equivalent to about 3 molar equivalents, per 1 mol of compound (II).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0) and the like) and the like, and a ligand (e.g., 2,2'-bis(diphenylphosphino)-1,1'-binaphthyl, 2,2'-bis(di-p-tolylphosphino)-1,1'-binaphthyl, 2-dicyclohexylphosphino-2',4',6'-triisopropyl-1,1'-biphenyl, triphenylphosphine, tri-tert-butylphosphine and the like) may be added as necessary. While the amount of the catalyst to be used varies depending on the kind of the catalyst, it is generally about 0.0001-about 1 molar equivalent, preferably about 0.01-about 0.5 molar equivalent, per 1 mol of compound (II). The amount of the ligand to be used is generally about 0.0001-about 4 molar equivalents, preferably about 0.01-about 2 molar equivalents, per 1 mol of compound (II).

Examples of the base to be used include organic amines (e.g., trimethylamine, triethylamine, diisopropylamine, N-methylmorpholine, 1,8-diazabicyclo[5.4.0]undec-7-ene, pyridine, N,N-dimethylaniline and the like), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydrides (potassium hydride, sodium hydride and the like), alkali metal alkoxides (sodium methoxide, sodium ethoxide, sodium-tert-butoxide, potassium-tert-butoxide and the like), alkali disilazides (e.g., lithium disilazide, sodium disilazide, potassium disilazide and the like) and the like. Among these, metal hydrides (potassium hydride, sodium hydride and the like); alkali metal alkoxides such as sodium-tert-butoxide, potassium-tert-butoxide and the like; and the like are preferable. The amount of the base to be used is generally about 0.1-about 10 molar equivalents, preferably about 1-about 5 molar equivalents, per 1 mol of compound (II).

The solvent to be used may be any as long as it does not adversely influence the reaction and, for example, hydrocarbons (e.g., benzene, toluene, xylene and the like), halogenated hydrocarbons (e.g., chloroform, 1,2-dichloroethane and the like), nitriles (e.g., acetonitrile and the like), ethers (e.g., dimethoxyethane, tetrahydrofuran and the like), aprotic polar solvents (e.g., N,N-dimethylformamide, dimethyl sulfoxide, hexamethylphosphoramide and the like), a mixture thereof and the like can be mentioned. The amount of these solvents to be used is generally 1- to 100-fold volume relative to compound (II).

The reaction temperature is generally about −10° C.-about 200° C., preferably about 0° C.-about 150° C. The reaction time is generally about 0.5-about 48 hr, preferably about 0.5-about 16 hr.

By this step, a compound represented by the formula (IV) (hereinafter to be referred to as compound (IV)) can also be converted to a compound represented by the formula (V) or a salt thereof (hereinafter to be referred to as compound (V)) in the below-mentioned method B. Compound (IV) can be produced from a corresponding compound by a method known per se to those of ordinary skill in the art.

(Step 2)

In this step, the tert-butoxycarbonyl group of compound (III) is removed to convert the compound to a compound represented by the formula (Ia) or a salt thereof (hereinafter to be referred to as compound (Ia)). While this reaction can be performed by a method known per se, it is generally performed by reacting acid in a solvent that does not adversely influence the reaction.

Examples of the acid to be used include hydrochloric acid, hydrobromic acid, sulfuric acid, trifluoroacetic acid, trifluoromethanesulfonic acid, hydrogen chloride and the like. The amount of the acid to be used is preferably about 1-about 100 mol, per 1 mol of compound (III).

Examples of the solvent that does not influence the reaction include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture of two or more kinds thereof at an appropriate ratio. The amount of these solvents to be used is, for example, generally 1- to 100-fold volume relative to compound (III).

The reaction temperature is generally about −50° C.-about 250° C., preferably 0° C.-120° C. The reaction time is generally about 0.5-about 24 hr.

The thus-obtained compound (Ia) can be isolated and purified by a known separation and purification means, for example, concentration, concentration under reduced pressure, solvent extraction, crystallization, recrystallization, phase transfer, chromatography and the like.
(Method B)
(Step 3)

In this step, the benzyl group of compound (V) is removed to convert the compound to a compound represented by the formula (Ib) or a salt thereof (hereinafter to be referred to as compound (Ib)).

Examples of the method for the removal of the benzyl group include a method known per se or the method described in Wiley-InterScience, 1999, "Protective Groups in Organic Synthesis, 3rd Ed." (Theodara W. Greene, Peter G. M. Wuts) and the like, or a method analogous thereto. For example, a catalytic hydrogenation reaction, and a treatment method with acid halide and the like can be mentioned.

The catalytic hydrogenation reaction can be performed in the presence of a catalyst under a hydrogen atmosphere. Examples of the catalyst include palladiums (e.g., palladium carbon, palladium hydroxide carbon, palladium oxide etc., and the like), nickels (e.g., developed nickel catalyst and the like), platinums (e.g., platinum oxide, platinum carbon and the like), rhodiums (e.g., rhodium carbon and the like) and the like. The amount thereof to be used is about 0.001-about 1 molar equivalent, preferably about 0.01-about 0.5 molar equivalent, per 1 mol of compound (V).

The catalytic hydrogenation reaction is generally performed in a solvent inert to the reaction. Examples of such solvent include alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), carboxylic acids (e.g., acetic acid and the like), water, and a mixture thereof. The amount of these solvents to be used is generally 1- to 100-fold volume relative to compound (V).

The hydrogen pressure under which the reaction is performed is generally about 1-about 50 atm, preferably about 1-about 10 atm. In addition, as a hydrogen source, formic acid, amine formate salt, phosphinate, hydrazine and the like may be used instead of hydrogen gas.

The reaction temperature is generally about 0° C.-about 150° C., preferably about 20° C.-about 100° C. The reaction time is generally about 5 min-about 72 hr, preferably about 0.5 hr-about 40 hr.

For the treatment method with acid halide, 1-chloroethy chloroformate, 2,2,2-trichloro-1,1-dimethylethyl chloroformate, β-trimethylsilylethyl chloroformate and the like are used. Among these, a method using 1-chloroethyl chloroformate is preferable. The amount of acid halide to be used is about 1-about 10 molar equivalents, preferably about 1-about 2 molar equivalents, per 1 mol of compound (V).

The reaction is generally performed in a solvent inert to the reaction. Examples of such solvent include hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide and the like), nitriles (e.g., acetonitrile and the like) and a mixture thereof. The amount of these solvents to be used is generally 1- to 100-fold volume relative to compound (V).

The reaction temperature is generally about −80° C.-about 150° C., preferably about 0° C.-about 100° C. The reaction time is generally about 5 min-about 72 hr, preferably about 0.5 hr-about 20 hr.

When 1-chloroethyl chloroformate is used, compound (V) is reacted with 1-chloroethyl chloroformate, and then treated with alcohol (e.g., methanol, ethanol and the like), an aqueous solution (e.g., aqueous sodium hydroxide solution and the like) or water to give compound (Ib). The reaction temperature therefor is generally about 0° C.-about 150° C., preferably about 5° C.-about 100° C. The reaction time is generally about 5 min-about 24 hr, preferably about 0.5 hr-about 5 hr.

By this step, a compound represented by the formula (XII) or a salt thereof (hereinafter to be referred to as compound (XII)) can be converted to a compound represented by the formula (Ic) or a salt thereof (hereinafter to be referred to as compound (Ic)) in method C, a compound represented by the formula (XIV) or a salt thereof (hereinafter to be referred to as compound (XIV)) can be converted to a compound represented by the formula (Id) or a salt thereof (hereinafter to be referred to as compound (Id)) in method D, a compound represented by the formula (XV) or a salt thereof (hereinafter to be referred to as compound (XV)) can be converted to a compound represented by the formula (Ie) or a salt thereof (hereinafter to be referred to as compound (Ie)) in method E, and a compound represented by the formula (XVI) or a salt thereof (hereinafter to be referred to as compound (XVI)) can be converted to a compound represented by the formula (If) or a salt thereof (hereinafter to be referred to as compound (If)) in method F.
(Method C)
(Step 4)

In this step, a compound represented by the formula (VI) or a salt thereof (hereinafter to be referred to as compound (VI)) is halogenated by reaction with a halogenating agent to convert the compound to a compound represented by the formula (VII) or a salt thereof (hereinafter to be referred to as compound (VII)). Compound (VI) may be a commercially available product, or can be produced from the corresponding compound by a method known per se to those of ordinary skill in the art.

The halogenating method can be performed according to a method known per se [e.g., Jikken Kagaku Koza 4th edition, vol. 22, p. 115 and the like] and, for example, performed in a solvent that does not adversely influence the reaction in the presence of a halogenating agent. Examples of the halogenating agent include thionyl chloride, phosphorus pentachloride, phosphorus oxychloride, oxalyl chloride and the like. The amount thereof to be used is about 1-about 10 molar equivalents, preferably about 1-about 3 molar equivalents, per 1 mol of compound (VI). The solvent to be used may be any as long as it does not adversely influence the reaction and, for example, hydrocarbons (e.g., benzene, toluene, xylene and the like), halogenated hydrocarbons (e.g., chloroform, 1,2-dichloroethane and the like), nitriles (e.g., acetonitrile and the like), ethers (e.g., dimethoxyethane, tetrahydrofuran and the like), aprotic polar solvents (e.g., N,N-dimethylformamide, dimethyl sulfoxide, hexamethylphosphoramide and the like) and a mixture thereof can be used. The amount of these solvents to be used is generally 1- to 100-fold volume relative to compound (VI). The reaction temperature is generally about −10° C.-about 200° C., preferably about 0° C.-about 150° C. The reaction time is generally about 0.5-about 48 hr, preferably about 0.5-about 16 hr. The thus-obtained compound (VII) can be isolated and purified by a known separation and purification means, for example, concentration, concentration under reduced pressure, solvent extraction, crystallization, recrystallization, phase transfer, chromatography and the like. In addition, compound (VII) may be used for the next reaction without isolation.
(Step 5)

In this step, compound (VII) is reacted with a compound represented by the formula (VIII) (hereinafter to be referred to as compound (VIII)) to give a compound represented by the formula (IX) or a salt thereof (hereinafter to be referred to as compound (IX)). Compound (VIII) may be a commercially available product, or can be produced from the corresponding compound by a method known per se to those of ordinary skill in the art.

The amount of compound (VIII) to be used is generally about 1 molar equivalent to about 10 molar equivalents, preferably about 1 molar equivalent to about 2 molar equivalents, per 1 mol of compound (VII).

The above-mentioned reaction is generally carried out in a solvent that does not adversely influence the reaction, and a base may be added to promote the reaction.

Examples of the solvent include hydrocarbons (e.g., benzene, toluene etc.), ethers (e.g., diethyl ether, dioxane, tetrahydrofuran etc.), esters (e.g., ethyl acetate etc.), halogenated hydrocarbons (e.g., chloroform, dichloromethane etc.), amides (e.g., N,N-dimethylformamide etc.), aromatic amines (e.g., pyridine etc.), water and the like. These solvents may be used in a mixture of two or more kinds thereof at an appropriate ratio. The amount of these solvents to be used is generally 1- to 100-fold volume relative to compound (VII).

Examples of the base include alkali metal hydroxides (e.g., sodium hydroxide, potassium hydroxide etc.), hydrogen carbonates (e.g., sodium hydrogen carbonate, potassium hydrogen carbonate etc.), carbonates (e.g., sodium carbonate, potassium carbonate etc.), acetates (e.g., sodium acetate etc.), tertiary amines (e.g., trimethylamine, triethylamine, N-methylmorpholine etc.), aromatic amines (e.g., pyridine, picoline, N,N-dimethylaniline etc.) and the like. The amount of the base to be used is generally about 1 molar equivalent to about 100 molar equivalents, preferably about 1 molar equivalent to about 5 molar equivalents, per 1 mol of compound (VII).

The reaction temperature is generally about −80° C. to about 150° C., preferably about −80° C. to about 50° C., and the reaction time is generally about 0.1 hr to about 48 hr, preferably about 0.5 hr to about 16 hr.

The thus-obtained compound (IX) can be isolated and purified by a known separation and purification means, for example, concentration, concentration under reduced pressure, solvent extraction, crystallization, recrystallization, phase transfer, chromatography and the like. In addition, compound (IX) may be used for the next reaction without isolation.

(Step 6)

In this step, compound (IX) is subjected to an intramolecular ring closure reaction to give a compound represented by the formula (X) or a salt thereof (hereinafter to be referred to as compound (X)). This reaction is performed by a method known per se, and generally in the presence of a base and, where necessary, in a solvent that does not adversely influence the reaction.

Examples of the base include metal hydrides (e.g., potassium hydride, sodium hydride etc.), inorganic bases (e.g., alkali metal hydroxides such as lithium hydroxide, sodium hydroxide, potassium hydroxide etc.; alkali metal hydrogen carbonates such as sodium hydrogen carbonate, potassium hydrogen carbonate etc.; alkali metal carbonates such as sodium carbonate, potassium carbonate etc.; alkoxides such as sodium methoxide, sodium ethoxide etc., and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridine, pyridazine, 4-dimethylaminopyridine etc.) and the like. Of these, metal hydrides such as sodium hydride and the like are preferable. While the amount of the base to be used varies depending on the kind of the solvent and other reaction conditions, it is generally about 0.1 molar equivalent to about 10 molar equivalents, preferably about 0.1 molar equivalent to about 5 molar equivalents, per 1 mol of compound (IX).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture of two or more kinds thereof at an appropriate ratio. The amount of these solvents to be used is generally 1- to 100-fold volume relative to compound (IX).

The reaction temperature is generally within the range of about −50° C. to about 200° C., preferably about 0° C. to about 150° C. While the reaction time varies depending on the kind of compound (IX), reaction temperature and the like, it is generally about 0.1 hr to about 100 hr, preferably about 0.5 hr to about 24 hr.

The thus-obtained compound (X) can be isolated and purified by known separation and purification means, for example, concentration, concentration under reduced pressure, solvent extraction, crystallization, recrystallization, phase transfer, chromatography and the like. In addition, compound (X) may be used for the next reaction without isolation.

(Step 7)

In this step, compound (X) is reacted with phenol, alcohol represented by the formula: $R^1$—OH wherein $R^1$ is as defined above, or a salt thereof, and subjected to phenoxylation or alkoxylation reaction to give a compound represented by the formula (XI) or a salt thereof (hereinafter to be referred to as compound (XI)). This reaction is performed by a method known per se [e.g., J. Am. Soc. Chem., 2005, vol. 127, page 201 and the like] generally in the presence of a base and, where necessary, in a solvent that does not influence the reaction.

The amount of phenol, alcohol or a salt thereof to be used is generally about 1 molar equivalent to about 100 molar equivalents, preferably about 1 molar equivalent to about 3 molar equivalents, per 1 mol of compound (X).

Examples of the base include metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like etc.), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridine, pyridazine, 4-dimethylaminopyridine etc.) and the like. Among these, metal hydrides such as sodium hydride and the like are preferable. While the amount of the base to be used varies depending on the kind of the solvent and other reaction conditions, it is generally about 0.1 molar equivalent to about 10 molar equivalents, preferably about 0.1 molar equivalent to about 5 molar equivalents, per 1 mol of compound (X).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), and the like. These solvents may be used in a mixture of two or more kinds thereof at an appropriate ratio. The amount of these solvents to be used is generally 1- to 100-fold volume relative to compound (X).

The reaction temperature is generally within the range of about −50° C. to about 300° C., preferably about 0° C. to about 200° C. While the reaction time varies depending on the kind of compound (X), reaction temperature and the like, it is generally about 0.1 hr to about 100 hr, preferably about 0.5 hr to about 36 hr.

The thus-obtained compound (XI) can be isolated and purified by known separation and purification means, for example, concentration, concentration under reduced pressure, solvent extraction, crystallization, recrystallization, phase transfer, chromatography and the like. In addition, compound (XI) may be used for the next reaction without isolation.

(Step 8)

In this step, compound (XI) is subjected to a reduction reaction to give compound (XII). This reaction can be performed by a method known per se generally in the presence of a reducing agent and, where necessary, in a solvent that does not adversely influence the reaction.

Examples of the reducing agent include aluminum reagents (e.g., lithium aluminum hydride ($LiAlH_4$), diisobutylaluminum hydride (DIBAL-H), sodium bis(2-methoxyethoxy)aluminum hydride (Red-Al), alane ($AlH_3$) etc.), boron reagents (e.g., borane ($BH_3$), 9-borabicyclo[3.3.1]nonane (9-BBN), sodium borohydride ($NaBH_4$), sodium cyanoborohydride ($NaBH_3CN$), sodium triacetoxyborohydride ($NaBH(OAc)_3$) etc.) and the like. Of these, lithium aluminum hydride and borane are preferable. While the amount of the reducing agent to be used varies depending on the kind of the solvent and other reaction conditions, it is generally about 1 molar equivalent to about 10 molar equivalents, preferably about 1 molar equivalent to about 5 molar equivalents, per 1 mol of compound (XI).

Examples of the solvent that does not adversely influence the reaction include alcohols (e.g., methanol, ethanol, propanol, 2-propanol, butanol, isobutanol, tert-butanol etc.), ethers (e.g., diethyl ether, diisopropyl ether, tert-butyl methyl ether, tetrahydrofuran, dioxane, dimethoxyethane etc.), carboxylic acid (e.g., acetic acid, trifluoroacetic acid etc.) and the like. These solvents may be used in a mixture of two or more kinds thereof at an appropriate ratio. The amount of these solvents to be used is generally 1- to 100-fold volume relative to compound (XI).

The reaction temperature is generally within the range of about −80° C. to about 200° C., preferably about −80° C. to about 100° C. While the reaction time varies depending on the kind of compound (XI), reaction temperature and the like, it is generally about 0.1 hr to about 100 hr, preferably about 0.5 hr to about 24 hr.

The thus-obtained compound (XII) can be isolated and purified by a known separation and purification means, for example, concentration, concentration under reduced pressure, solvent extraction, crystallization, recrystallization, phase transfer, chromatography and the like. In addition, compound (XII) may be used for the next reaction without isolation.

By this step, a compound represented by the formula (XIII) or a salt thereof (hereinafter to be referred to as compound (XIII)) can also be converted to compound (XIV) in the below-mentioned method D.

(Method D)

(Step 9)

In this step, compound (X) is reacted with thiol represented by the formula: $R^2$—SH wherein $R^2$ is as defined above, or a salt thereof and subjecting to a sulfanylation reaction to give compound (XIII).

This reaction can be performed by a method known per se generally in the presence of a base and, where necessary, in a solvent that does not adversely influence the reaction.

The amount of thiol or a salt thereof to be used is generally about 1 molar equivalent to about 100 molar equivalents, preferably about 1 molar equivalent to about 3 molar equivalents, per 1 mol of compound (X).

Examples of the base include metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkoxides such as sodium methoxide, sodium ethoxide etc. and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridine, pyridazine, 4-dimethylaminopyridine etc.) and the like. Of these, metal hydrides such as sodium hydride and the like are preferable. While the amount of the base to be used varies depending on the kind of the solvent and other reaction conditions, it is generally about 0.1 molar equivalent to about 10 molar equivalents, preferably about 0.1 molar equivalent to about 5 molar equivalents, per 1 mol of compound (X).

Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture of two or more kinds thereof at an appropriate ratio. The amount of these solvents to be used is generally 1- to 100-fold volume relative to compound (X).

The reaction temperature is generally within the range of about −50° C. to about 300° C., preferably about 0° C. to about 200° C. While the reaction time varies depending on the kind of thiol, reaction temperature and the like, it is generally about 0.1 hr to about 100 hr, preferably about 0.5 hr to about 36 hr. The thus-obtained compound (XIII) can be isolated and purified by known separation and purification means, for example, concentration, concentration under reduced pressure, solvent extraction, crystallization, recrystallization, phase transfer, chromatography and the like. In addition, compound (XIII) may be used for the next reaction without isolation.

(Method E)

(Step 10)

In this step, compound (XIV) is reacted with an oxidant and subjected to an oxidation reaction to give compound (XV). This reaction can be performed by a method known per se and, where necessary, in a solvent that does not adversely influence the reaction.

Examples of the oxidant include hydrogen peroxide, m-chloroperbenzoic acid, oxone (registered trade mark) and the like. Of these, m-chloroperbenzoic acid and oxone (registered trade mark) are preferable. While the amount of the oxidant to be used varies depending on the kind of the solvent and other reaction conditions, it is generally about 0.5 molar equivalent to about 1 molar equivalent, preferably about 0.7 molar equivalent to about 1 molar equivalent, per 1 mol of compound (XIV).

Examples of the solvent that does not adversely influence the reaction include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), water and the like. These solvents may be used in a mixture of two or more kinds thereof at an appropriate ratio. The amount of these solvents to be used is generally 1- to 100-fold volume relative to compound (XIV).

Where necessary, this reaction may be performed under acidic conditions with acetate, sulfate, phosphate buffer and the like. By performing the reaction under the acidic conditions, oxidation of nitrogen atom on the pyridooxazepine ring can be suppressed, and an effect of improved selectivity of sulfur atom on the sulfanyl group to oxidation can be expected.

The reaction temperature is generally within the range of about −50° C. to about 100° C., preferably about −10° C. to about 30° C. While the reaction time varies depending on the kind of thiol, reaction temperature and the like, it is generally about 0.1 hr to about 100 hr, preferably about 0.5 hr to about 36 hr.

The thus-obtained compound (XV) can be isolated and purified by known separation and purification means, for example, concentration, concentration under reduced pressure, solvent extraction, crystallization, recrystallization, phase transfer, chromatography and the like. In addition, compound (XV) may be used for the next reaction without isolation.

(Method F)
(Step 11)

In this step, compound (XIV) is reacted with an oxidant and subjected to an oxidation reaction to give compound (XVI). This reaction can be performed by a method known per se, and where necessary, in a solvent that does not adversely influence the reaction. Examples of the oxidant include hydrogen peroxide, m-chloroperbenzoic acid, oxone (registered trade mark) and the like. Among these, m-chloroperbenzoic acid and oxone (registered trade mark) are preferable. While the amount of the oxidant to be used varies depending on the kind of the solvent and other reaction conditions, it is generally about 2 molar equivalents to about 10 molar equivalents, preferably about 2 molar equivalents to about 3 molar equivalents, per 1 mol of compound (XIV).

Examples of the solvent that does not adversely influence the reaction include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), water and the like. These solvents may be used in a mixture of two or more kinds thereof at an appropriate ratio. The amount of these solvents to be used is generally 1- to 100-fold volume relative to compound (XIV).

Where necessary, this reaction may be performed under acidic conditions with acetate, sulfate, phosphate buffer, and the like. By performing the reaction under the acidic conditions, oxidation of nitrogen atom on the pyridooxazepine ring can be suppressed, and an effect of improved selectivity of sulfur atom on the sulfanyl group to oxidation can be expected.

The reaction temperature is generally within the range of about −50° C. to about 100° C., preferably about −10° C. to about 30° C. While the reaction time varies depending on the kind of thiol, reaction temperature and the like, it is generally about 0.1 hr to about 100 hr, preferably about 0.5 hr to about 36 hr.

The thus-obtained compound (XVI) can be isolated and purified by known separation and purification means, for example, concentration, concentration under reduced pressure, solvent extraction, crystallization, recrystallization, phase transfer, chromatography and the like. In addition, compound (XVI) may be used for the next reaction without isolation.

Compound (I) produced by such method can be isolated and purified by a typical separation means such as recrystallization, distillation, chromatography, etc.

When compound (I) contains an optical isomer, a stereoisomer, a regioisomer or a rotamer, these are also encompassed in compound (I), and can be obtained as a single product according to synthesis methods or separation methods known per se (e.g., concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) a Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxyl, or primary or secondary amino in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers in the ester form or in the amide form, respectively. When compound (I) has carboxylic acid, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

The compound (I) may be a crystal.

The crystal of the compound (I) can be produced by crystallization of compound (I) according to crystallization methods known per se.

Examples of the crystallization method include a method of crystallization from a solution, a method of crystallization from vapor, a method of crystallization from the melts and the like.

The "method of crystallization from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "method of crystallization from vapor" is, for example, a vaporization method (a sealed tube method, a gas stream method), a gas phase reaction method, a chemical transportation method and the like.

The "method of crystallization from the melts" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method of dissolving compound (I) in a suitable solvent (e.g., alcohols such as methanol, ethanol, etc., and the like) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical composition.

In the present specification, specific optical rotation ($[\alpha]_D$) means a specific optical rotation measured with, for example, a polarimeter (JASCO Corporation), P-1030 type polarimeter (No. AP-2)) and the like.

In the present specification, the melting point means a melting point measured using, for example, a micro melting point apparatus (YANACO, MP-500D), a DSC (differential scanning calorimetry) apparatus (SEIKO, EXSTAR6000) and the like.

A prodrug of the compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I) or a prodrug thereof (to be abbreviated as "the compound of the present invention" in the present specification) has a superior serotonin $5-HT_{2C}$ receptor activating action.

In addition, the compound of the present invention is low toxic and safe. Particularly, the compound is useful since it is phototoxicity-free.

Accordingly, the compound of the present invention having a superior serotonin $5-HT_{2C}$ receptor activating action is useful as a prophylactic or therapeutic drug for all serotonin $5-HT_{2C}$ associated diseases in mammals (e.g., mouse, rat, hamster, rabbit, cat, dog, bovine, sheep, monkey, human and the like), for example, (1) lower urinary tract diseases (including all diseases having lower urinary tract symptoms described below including, for example, overactive bladder, benign prostatic hyperplasia, interstitial cystitis, chronic prostatitis etc.):
storage symptom (e.g., diurnal urinary frequency, nocturnal urinary frequency, urinary urgency, urinary incontinence, stress urinary incontinence, urge urinary incontinence, mixed urinary incontinence, enuresis, nocturnal enuresis, continuous urinary incontinence, other urinary incontinence, enhanced, decreased or missing bladder sensation etc.), voiding symptom (e.g., weak urinary stream (or slow stream), split urinary stream, spraying stream, intermittent urinary stream, voiding postponement, straining at urination, terminal dribbling etc.), post-micturition symptom (e.g., sense of residual urine, post-micturition dribble etc.), symptom due to sexual intercourse (e.g., coital pain, vaginal dryness, urinary incontinence etc.), symptom due to pelvic organ prolapse (e.g., foreign body sensation, lumbago etc.), genital organ pain or lower urinary tract pain (e.g., cystalgia, urethral pain, pudendalgia, vaginodynia, scrotal pain, perineal pain, pelvic pain etc.), genital organ or urinary tract pain syndrome (e.g., cystalgia syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (e.g., overactive bladder syndrome, lower urinary tract symptom suggesting bladder outlet obstruction etc.), polyuria, urolithiasis (e.g., ureteral calculus, urethral calculus) and the like;
(2) metabolic diseases [for example, diabetes (e.g., insulin dependent diabetes, diabetic complications, diabetic retinopathy, diabetic microangiopathy, diabetic neuropathy etc.), impaired glucose tolerance, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity], benign prostatic hyperplasia, sexual dysfunction and the like];
(3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), central nervous system and peripheral nerve disorders (e.g., head trauma, spinal damage, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorder (e.g., disorders such as cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation, sleep disorder etc.];

(4) genital insufficiency diseases [for example, male erectile dysfunction, dyspermia, female genital insufficiency etc.];
(5) digestive organ diseases [for example, irritable bowel syndrome, inflammatory intestinal disease, ulcerative colitis, Crohn's disease, diseases caused by a spiral urease-positive gram-negative bacterium (e.g., *Helicobacter pylori*, etc.) (e.g., gastritis, gastric ulcer, etc.), gastric cancer, postgastrostomy disorder, indigestion, esophageal ulcer, pancreatitis, polyp of the colon, cholelithiasis, hemorrhoids, peptic ulcer, situational ileitis, gluttony, constipation, diarrhea, borborygmus, etc.];
(6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ocular disease, etc.];
(7) bone and articular diseases [for example, rheumatoid arthritis (e.g., rheumatoid arthritis), arthritis deformans, rheumatoid myelitis, osteoporosis, abnormal growth of cells and the like, bone fracture, bone refracture, osteomalacia, osteopenia, Paget's disease of bone, rigid myelitis, articular tissue destruction by gonarthrosis deformans and similar diseases thereto, etc.];
(8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough, etc.];
(9) infectious diseases [for example, HIV infectious diseases, virus infectious diseases due to cytomegalo virus, influenza virus, herpes virus and the like, *rickettsia* infectious diseases, bacterial infectious diseases, sexually-transmitted diseases, carinii pneumonia, *Helicobacter pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.];
(10) cancers [for example, primary, metastatic or recurrent breast cancer, prostatic cancer, pancreatic cancer, gastric cancer, lung cancer, colorectal cancer (e.g., colon cancer, rectal cancer, anal cancer), esophagus cancer, duodenal cancer, head and neck cancer (e.g., cancer of the tongue, pharynx cancer, laryngeal cancer), brain tumor, schwannoma, non-small cell lung cancer, small cell lung cancer, liver cancer, kidney cancer, biliary tract cancer, uterine cancer (e.g., uterine body cancer, cervical cancer), ovary cancer, urinary bladder cancer, skin cancer, Hemangioma, malignant lymphoma, malignant melanoma, thyroid cancer, bone tumor, Hemangioma, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia and the like, Hodgkin's disease, etc.];
(11) circulatory diseases [for example, acute coronary artery syndromes (e.g., acute myocardial infarction, unstable angina, etc.), peripheral arterial occlusion, Raynaud's disease, Buerger's disease, restenosis after coronary-artery intervention (percutaneous transluminal coronary angioplasty (PTCA), directional coronary atherectomy (DCA), stenting, etc.), restenosis after coronary-artery bypass operation, restenosis after intervention (e.g., angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (e.g., acute cardiac failure, chronic cardiac failure including congestive cardiac failure), arrhythmia, progress of atherosclerotic plaque, thrombosis, hypertension, hypertensive tinnitus, hypotension, etc.];

(12) pains [e.g., headache, migraine, neuralgia, pelvic organ pain (including bladder pain), etc.];

(13) autoimmune diseases [for example, collagen disease, systemic lupus erythematosus, scleroderma, polyarteritis, myasthenia gravis, multiple sclerosis, Sjogren's syndrome, Behcet's disease, etc.];

(14) hepatic diseases [e.g., hepatitis (including chronic hepatitis), cirrhosis, interstitial hepatic diseases, etc.];

(15) pancreatic diseases [e.g., pancreatitis (including chronic pancreatitis), etc.];

(16) renal diseases [e.g., nephritis, glomerulonephritis, glomerulosclerosis, renal failure, thrombotic microangiopathy, dialysis complications, organ disorders including nephropathia by radiation, diabetic nephropathy, etc.];

(17) endocrine diseases [e.g., Addison's disease, Cushing's syndrome, melanocytoma, primary aldosteronism, etc.];

(18) other diseases [for example,
(a) transplant rejection [e.g., posttransplantational rejection, posttransplantational polycythemia, hypertension, organ disorder and/or vascular hypertrophy, graft-versus-host disease, etc.];
(b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.];
(c) gynecologic diseases [for example, climacteric disorder, gestational toxicosis, endometriosis, hysteromyoma, ovarian disease, mammary disease, premenstrual syndrome, pelvic organ prolapse, rectal prolapsed, cystocele, enterocele and the like];
(d) dermatic diseases [e.g., keloid, hemangioma, psoriasis, pruritus, etc.];
(e) ophthalmic diseases [e., glaucoma, ocular hypertension disease, etc.];
(f) otolaryngological diseases [e.g., Menuel syndrome, tinnitus, gustation disorder, dizziness, disequilibrium, dysphagia, etc.];
(g) diseases due to environmental and/or occupational factors (e.g., radiation disorder, disorders by ultraviolet ray/infrared ray/laser ray, altitude sickness, etc.);
(h) ataxia, stiffness, tremor, motion impairment, akinesia etc.;
(i) chronic fatigue syndrome;
(j) sudden infant death syndrome;
(k) hiccup;
(l) diseases causing palpitation, vertigo, heartburn, etc.]; and the like.

In addition, the serotonin 5-$HT_{2C}$ receptor activators including the compound of the present invention can also be used for the prophylaxis or treatment of diseases caused by prolapses of an organ from its normal position due to weakened pelvic floor muscles such as cystocele, enterocele and the like (e.g., proctocele and the like).

Pelvic organ prolapse, rectal prolapse, cystocele and enterocele are diseases characterized by the protrusion of bladder, uterus, small intestine, rectal or the like beyond the vaginal orifice or the rectal orifice due to the lack of the contractile force of the pelvic floor muscles.

Accordingly, the present invention provides a medicament for the above-mentioned diseases, comprising the compound of the present invention.

The medicament of the present invention is particularly useful as, among these diseases, a serotonin 5-$HT_{2C}$ receptor activator, and is also useful as a drug for the prophylaxis or treatment of lower urinary tract symptom, obesity and/or organ prolapse.

A preparation containing the compound of the present invention may be any of solid preparations including powder, granule, tablet, capsule, orally disintegrable films and the like, and liquid agents such as syrup, emulsion, injection and the like.

The preparation of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the agent of the present invention may be formed into a sustained-release preparation containing an active ingredient and a biodegradable polymer compound. The sustained-release preparation can be produced according to the method described in JP-A-9-263545.

In the preparation of the present invention, while the content of the compound of the present invention varies depending on the form of the preparation, it is generally 0.01-100 wt %, preferably 0.1-50 wt %, more preferably about 0.5-20 wt %, in an amount of compound (I) relative to the whole preparation.

When the compound of the present invention is used in the above-mentioned pharmaceutical products, it may be used alone, or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by ordinary methods. It can be formulated into the solid preparations such as powders, fine granules, granules, tablets, capsules, etc., or into the liquid preparations such as injections, etc., and can be administered orally or parenterally. When the compound of the present invention is formed as a preparation for topical administration and administered, it can also be directly administered to the affected part of an articular disease. In this case, an injection is preferable. It can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, the compound of the present invention is formulated into an aqueous suspension with a dispersing agent (e.g., surfactants such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound of the present invention together with vegetable oil such as sesame oil, corn oil and the like or a mixture thereof with a phospholipid such as lecithin and the like, or medium-chain triglyceride (e.g., miglyol 812 etc.) to give an injection to be actually used.

The medicament of the present invention can be used along with other medicament.

As a drug that can be blended or combined with the compound of the present invention (hereinafter to be abbreviated as concomitant drug), the following drugs and the like can be used.

(1) Other Drugs for Treating Stress Urinary Incontinence

Adrenaline α1 receptor agonists (e.g., ephedrine hydrochloride, midodrine hydrochloride), adrenaline β2 receptor agonists (e.g., Clenbuterol), noradrenaline uptake inhibitory substances, noradrenaline and serotonin uptake inhibitory substances (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Agent for Treating Diabetes

Insulin preparations. [e.g., animal insulin preparations extracted from the bovine or swine pancreas; human insulin preparations synthesized by a genetic engineering technique using Escherichia coli or a yeast; insulin zinc; protamine zinc insulin; a fragment or a derivative of insulin (e.g., INS-1, etc.) and the like], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(3) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(4) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors, fibrate compounds having triglyceride lowering action (e.g., bezafibrate, clofibrate, simfibrate, clinofibrate, etc.) and the like.

(5) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(6) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.) and the like.

(7) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(8) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(9) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(10) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentaenoic acid etc.) [British Journal of Cancer, vol. 68, pp. 314-318, 1993], growth hormones, IGF-1, and antibodies to the cachexia-inducing factors such as TNF-α, LIF, IL-6 and oncostatin M, and the like.

(11) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(12) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.) and the like, preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

NK-2 receptor antagonists include, for example, piperidine derivatives such as GR159897, GR149861, SR48968 (saredutant), SR144190, YM35375, YM38336, ZD7944, L-743986, MDL105212A, ZD6021, MDL105172A, SCH205528, SCH62373, R-113281, etc., perhydroisoindole derivatives such as RPR-106145, etc., quinoline derivatives such as SB-414240, etc., pyrrolopyrimidine derivatives such as ZM-253270, etc., pseudopeptide derivatives such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

In combination of the compound of the present invention and the concomitant drug, the administration time of the compound of the present invention and the concomitant drug is not restricted, and the compound of the present invention or a pharmaceutical composition thereof and the concomitant drug or a pharmaceutical composition thereof can be administered to the administration subject simultaneously, or may be administered at different times. The dosage of the concomitant drug may be determined according to the dose clinically used, and can be appropriately selected depending on the administration subject, administration route, disease, combination and the like.

The concomitant administration mode is not particularly restricted, and it is sufficient that the compound of the present invention and the concomitant drug are combined in administration. Examples of such administration mode include the following methods:

(1) The compound of the present invention or a pharmaceutical composition thereof and the concomitant drug are simultaneously produced to give a single preparation which is administered.

(2) The compound of the present invention or a pharmaceutical composition thereof and the concomitant drug or a pharmaceutical composition thereof are separately produced to give two kinds of preparations which are administered simultaneously by the same administration route.

(3) The compound of the present invention or a pharmaceutical composition thereof and the concomitant drug or a pharmaceutical composition thereof are separately produced to give two kinds of preparations which are administered by the same administration route at different times.

(4) The compound of the present invention or a pharmaceutical composition thereof and the concomitant drug or a pharmaceutical composition thereof are separately produced to give two kinds of preparations which are administered simultaneously by different administration routes.

(5) The compound of the present invention or a pharmaceutical composition thereof and the concomitant drug or a pharmaceutical composition thereof are separately produced to give two kinds of preparations which are administered by different administration routes at different times (e.g., the compound of the present invention or a pharmaceutical composition thereof; the concomitant drug or a pharmaceutical composition thereof are administered in this order, or in the reverse order).

The mixing ratio of the compound of the present invention and a concomitant drug in the combination drug of the present invention can be appropriately determined according to the subject of administration, administration route, disease and the like.

For example, while the content of the compound of the present invention in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when the compound of the present invention and the concomitant drug are independently formulated.

While the dose varies depending on the kind of the compound of the present invention, administration route, symptom, age of patients and the like, for example, for oral administration to an adult patient with stress urinary incontinence and/or obesity, it is about 0.005 to 50 mg, preferably about 0.05 to 10 mg, more preferably about 0.2 to 4 mg/kg body weight/day as compound (I), which can be administered in 1 to about 3 portions.

When the pharmaceutical composition of the present invention is a sustained-release preparation, the dose varies depending on the kind and content of the compound of the present invention, dosage form, period of sustained drug release, subject animal of administration (e.g., mammals such as human, rat, mouse, cat, dog, rabbit, bovine, swine and the like) and administration object. For parenteral administration, for example, about 0.1 to about 100 mg of the compound of the present invention only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the concomitant drug may be administered before administering the compound of the present invention, or vice versa. In case of staggered administration, the time interval varies depending on the active ingredients to be administered, a formulation and an administration route. For example, if the concomitant drug is administered first, the compound of the present invention may be administered 1 minute to 3 days, preferably 10 minutes to 1 day, more preferably 15 minutes to 1 hour after administering the concomitant drug. If the compound of the present invention is administered first, the concomitant drug may be administered 1 minute to 1 day, preferably 10 minutes to 6 hours, more preferably 15 minutes to 1 hour after administering the compound of the present invention.

The pharmaceutical composition of the present invention is low toxic and can be used safely. Particularly, the following Example compounds are superior in the absorbability by oral administration, and can be advantageously used for an oral preparation. In addition, the composition is also superior since it is phototoxicity-free.

EXAMPLES

The present invention is further described in detail in with Examples, Experimental Examples and Formulation Examples which are not intended to restrict the invention and may be modified without departing from the scope of the invention.

In Examples, column chromatography was performed using Purif-8 or Purif-α2 manufactured by MORITEX and under observation by a UV detector. The silica gel used for column chromatography was Purif-Pack manufactured by MORITEX. The room temperature generally means a temperature of from about 10° C. to 30° C. Furthermore, sodium sulfate or magnesium sulfate was used for drying the extract solution.

The abbreviations in Examples and Experimental Examples mean the following.
LC: liquid chromatography
MS: mass spectrometry spectrum
ESI: electrospray method
M: molecular weight
NMR: nuclear magnetic resonance spectrum
Hz: hertz
J: coupling constant
m: multiplet
q: quartet
t: triplet
d: doublet
dd: double doublet
s: singlet
br: broad
dt: double triplet
brs: broad singlet
Ac: acetyl group
$^t$Bu: tert-butyl group
Boc: tert-butyloxycarbonyl group
Et: ethyl group
Ph: phenyl group
N: normal concentration
MeOH: methanol
DMF: N,N-dimethylformamide
THF: tetrahydrofuran
DMSO: dimethyl sulfoxide
DMA: N,N-dimethylacetamide
DME: dimethoxyethane
TFA: trifluoroacetic acid
Boc$_2$O: di-tert-butyl bicarbonate
XPhos: dicyclohexyl(2',4',6'-triisopropylbiphenyl-2-yl)phosphine
Pd$_2$(dba)$_3$: tris(dibenzylideneacetone)dipalladium(0)
20% Pd(OH)$_2$/C: 20% palladium hydroxide/carbon
BINAP: 2,2'-bis(di-phenylphosphino)-1,1'-binaphthyl
(S)-tol-BINAP: (S)-(−)-2,2'-bis(di-para-tolylphosphino)-1,1'-binaphthyl LC-MS in Example 1 to Example 62 was measured under the following conditions.
Analysis by LC-MS
measurement device: Waters LC-MS system
HPLC: Agilent HP1100
MS: Micromass ZQ
HPLC conditions
column: CAPCELL PAK C18UG120, S-3 μM, 1.5×35 mm (Shiseido Co., Ltd.)
solvent: SOLUTION A; 0.05% trifluoroacetic acid-containing water, SOLUTION B; 0.05% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
injection volume: 2 μL, flow rate: 0.5 mL/min, detection method: UV220 nm
MS conditions
ionization method: ESI Purification by preparative HPLC in Example 1 to Example 62 was performed under the following conditions.
device: Gilson Inc. High-Throughput Purification System
column: CombiPrep ODS-A S-5 μm, 50×20 mm (YMC)
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLU- TION A/SOLUTION B=5/95), 6.50 min (SOLUTION A/SOLUTION B=95/5), 6.60 min (SOLUTION A/SOLUTION B=95/5)

flow rate: 25 mL/min, detection method: UV220 nm

Purification by high-resolution preparative HPLC in the following Examples 1 to 62 were carried out under the following conditions.

Instrument: Gilson high-throughput purification system

Column: Combiprep Hydrosphere C18, 50×20 mm (YMC)

Solvent: Solution A; water containing 0.1% trifluoroacetic acid, Solution B; acetonitrile containing 0.1% trifluoroacetic acid Gradient cycle: 0.00 min (Solution A/Solution B=98/2), 1.00 min (Solution A/Solution B=98/2), 5.20 min (Solution A/Solution B=60/40), 5.40 min (Solution A/Solution B=5/95), 6.40 min (Solution A/Solution B=5/95), 6.50 min (Solution A/Solution B=98/2), 6.60 min (Solution A/Solution B=98/2)

Flow rate: 20 mL/min, detection method: UV 220 nm

Example 1

8-tert-butoxy-2,3,4,5-tetrahydropyrido[3,2-f][1,4]oxazepine (Step 1)

A solution of 4-benzyl-8-chloro-2,3,4,5-tetrahydropyrido[3,2-f][1,4]oxazepine (1.0 g), $^t$BuONa (0.70 g) and BINAP (0.068 g) in toluene (10 mL) was deaerated with an argon gas, $Pd_2(dba)_3$ (0.050 g) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-tert-butoxy-2,3,4,5-tetrahydropyrido[3,2-f][1,4]oxazepine (0.81 g, 72%) as an colorless oil.

$^1$H-NMR (CDCl$_3$): δ1.57 (9H, s), 3.05 (2H, m), 3.65 (2H, s), 3.66 (2H, s) 4.21 (2H, m), 6.35 (1H, d, J=8.0 Hz), 7.21 (1H, d, J=8.0 Hz), 7.26-7.35 (5H, m)

(Step 2)

A mixture of the compound obtained in step 1 (0.81 g), 20% Pd(OH)$_2$/C (0.081 g) and methanol (10 mL) was stirred at 40° C. for 2 days under a hydrogen atmosphere. The insoluble material was removed by filtration, and the filtrate was concentrated under reduced pressure. The residue was purified by basic silica gel column chromatography (solvent gradient; 40→100% ethyl acetate/hexane) to give the title compound (0.16 g, 57%) as a colorless oil.

$^1$H-NMR (CDCl$_3$): δ1.56 (9H, s), 1.61 (1H, brs), 3.20-3.25 (2H, m), 3.86 (2H, s), 4.10-4.20 (2H, m), 6.35 (1H, d, J=7.9 Hz), 7.32 (1H, d, J=7.9 Hz)

Example 2

8-tert-butoxy-2,3,4,5-tetrahydropyrido[3,2-f][1,4]oxazepine succinate

To the compound obtained in Example 1 (0.39 g) was added 0.5 M succinic acid/methanol solution (1.9 mL), and the solvent was evaporated under reduced pressure. The obtained residue was recrystallized from methanol-diethyl ether to give the title compound (0.27 g, 46%) as a white powder.

$^1$H-NMR (DMSO-d$_6$): δ1.50 (9H, s), 2.38 (4H, s), 3.05-3.15 (2H, m), 3.45 (2H, brs), 3.80 (2H, s), 4.05-4.15 (2H, m), 6.35 (1H, d, J=8.0 Hz), 7.51 (1H, d, J=8.0 Hz), 9.39 (1H, brs)

MS (ESI+): 223 (M−C$_4$H$_6$C$_4$+H)

Example 3

8-isobutoxy-2,3,4,5-tetrahydropyrido[3,2-f][1,4]oxazepine hydrochloride (Step 1)

To a solution of isobutyl alcohol (0.16 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-isobutoxy-2,3-dihydropyrido[3,2-f][1,4]oxazepine-4(5H)-carboxylate (0.33 g, 58%) as a yellow oil.

$^1$H-NMR (CDCl$_3$): δ1.00 (6H, d, J=6.8 Hz), 1.42 (9H, s), 1.98-2.10 (1H, m), 3.75-3.85 (2H, m), 4.02 (2H, d, J=6.6 Hz), 4.21 (2H, brs), 4.34-4.43 (2H, m), 6.45 (1H, d, J=7.9 Hz), 7.39-7.49 (1H, m)

(step 2)

A mixture of the compound obtained in step 1 (0.33 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.22 g, 83%) as a white powder.

$^1$H-NMR (DMSO-d$_6$): δ0.95 (6H, d, J=6.7 Hz), 1.95-2.05 (1H, m), 3.46 (2H, brs), 3.96 (2H, d, J=6.7 Hz), 4.24 (2H, brs), 4.30-4.35 (2H, m), 6.61 (1H, d, J=8.1 Hz), 7.79 (1H, d, J=8.1 Hz), 9.64 (2H, brs)

MS (ESI+): 223 (M−HCl+H)

Example 4

8-isopropoxy-2,3,4,5-tetrahydropyrido[3,2-f][1,4]oxazepine hydrochloride (Step 1)

To a solution of isopropyl alcohol (0.081 mL) in toluene (2 mL) was added sodium hydride (0.084 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.30 g), (S)-tol-BINAP (0.022 g), Pd$_2$(dba)$_3$ (0.015 g) and toluene (2 mL) was added, and the resulting mixture was stirred at 100° C. for 16 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-isopropoxy-2,3-dihydropyrido[3,2-f][1,4]oxazepine-4(5H)-carboxylate (0.21 g, 64%) as a colorless oil.

$^1$H-NMR (CDCl$_3$): δ1.31 (6H, d, J=6.2 Hz), 1.42 (9H, s), 3.75-3.85 (2H, m), 4.21 (2H, brs), 4.34-4.43 (2H, m), 5.25-5.35 (1H, m), 6.39 (1H, d, J=7.9 Hz), 7.38-7.50 (1H, m)

(Step 2)

A mixture of the compound obtained in step 1 (0.21 g) and 4N hydrogen chloride/ethyl acetate (5 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. The residue was purified by basic silica gel column chromatography (solvent gradient; 0→40% ethyl acetate/hexane), and 4N hydrogen chloride/ethyl acetate was added. The precipitate was collected by filtration and recrystallized from ethanol-ethyl acetate to give the title compound (0.0050 g, 3%) as a white powder.

$^1$H-NMR (CD$_3$OD): δ1.31 (6H, d, J=6.1 Hz), 3.55-3.65 (2H, m), 4.32 (2H, s), 4.30-4.40 (2H, m), 4.86 (2H, s), 5.15-5.25 (1H, m), 6.55 (1H, d, J=8.1 Hz), 7.69 (1H, d, J=8.1 Hz)

MS (ESI+): 209 (M−HCl+H)

Example 5

8-isopropoxy-2,3,4,5-tetrahydropyrido[3,2-f][1,4]oxazepine 0.5 succinate

A mixture of the compound obtained in Example 4, step 1 (0.60 g), 4N hydrogen chloride/ethyl acetate (5 mL) and ethyl acetate (5 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. The residue was purified by basic silica gel column chromatography (solvent gradient; 0→40% ethyl acetate/hexane), 0.5M succinic acid/methanol solution was added, and the solvent was evaporated under reduced pressure. The obtained residue was recrystallized from ethyl acetate-hexane to give the title compound (0.032 g, 6%) as a white powder.

$^1$H-NMR (CDCl$_3$): δ1.32 (6H, d, J=6.2 Hz), 2.45 (2H, s), 3.35-3.40 (2H, m), 4.03 (2H, s), 4.27 (2H, brs), 5.20-5.30 (1H, m), 5.76 (2H, brs), 6.41 (1H, d, J=8.1 Hz), 7.44 (1H, d, J=8.1 Hz)

MS (ESI+): 209 (M−0.5C$_4$H$_6$C$_4$+H)

Example 6

8-(1,2-dimethylpropoxy)-2,3,4,5-tetrahydropyrido[3,2-f][1,4]oxazepine hydrochloride (Step 1)

To a solution of 3-methylbutan-2-ol (0.19 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(1,2-dimethylpropoxy)-2,3-dihydropyrido[3,2-f][1,4]oxazepine-4(5H)-carboxylate (0.36 g, 61%) as a yellow oil.

$^1$H-NMR (CDCl$_3$): δ0.94 (3H, d, J=6.8 Hz), 0.96 (3H, d, J=6.6 Hz), 1.23 (3H, d, J=6.2 Hz), 1.43 (9H, s), 1.83-1.95 (1H, m), 3.75-3.85 (2H, m), 4.21 (2H, brs), 4.34-4.43 (2H, m), 4.97 (1H, brs), 6.39 (1H, d, J=7.9 Hz), 7.30-7.50 (1H, m)

(Step 2)

A mixture of the compound obtained in step 1 (0.36 g) and 4N hydrogen chloride/ethyl acetate (10 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.15 g, 52%) as a white powder.

$^1$H-NMR (DMSO-d$_6$): δ0.90 (3H, d, J=6.8 Hz), 0.91 (3H, d, J=6.8 Hz), 1.17 (3H, d, J=6.2 Hz), 1.81-1.91 (1H, m), 3.47 (2H, brs), 4.20-4.40 (4H, m), 4.81-4.91 (1H, m), 6.56 (1H, d, J=8.1 Hz), 7.76 (1H, d, J=8.1 Hz), 9.50 (2H, brs)

MS (ESI+): 237 (M−HCl+H)

Example 7

8-(cyclopropylmethoxy)-2,3,4,5-tetrahydropyrido[3,2-f][1,4]oxazepine hydrochloride (Step 1)

To a solution of cyclopropylmethanol (0.14 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(cyclopropylmethoxy)-2,3-dihydropyrido[3,2-f][1,4]oxazepine-4(5H)-carboxylate (0.33 g, 59%) as a yellow oil.

$^1$H-NMR (CDCl$_3$): δ0.28-0.38 (2H, m), 0.55-0.65 (2H, m), 1.21-1.31 (1H, m), 1.42 (9H, s), 3.75-3.85 (2H, m), 4.09 (2H, d, J=7.1 Hz), 4.20 (2H, brs), 4.34-4.50 (2H, m), 6.48 (1H, d, J=7.9 Hz), 7.40-7.50 (1H, m)

(Step 2)

A mixture of the compound obtained in step 1 (0.33 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from methanol-ethanol-diisopropyl ether to give the title compound (0.14 g, 55%) as a white powder.

¹H-NMR (DMSO-d₆): δ0.25-0.38 (2H, m), 0.50-0.60 (2H, m), 1.15-1.25 (1H, m), 3.44-3.54 (2H, m), 4.02 (2H, d, J=7.2 Hz), 4.26-4.40 (4H, m), 6.63 (1H, d, J=8.2 Hz), 7.77 (1H, d, J=8.2 Hz), 9.21 (2H, brs)
MS (ESI+): 221 (M−HCl+H)

Example 8

8-(cyclobutyloxy)-2,3,4,5-tetrahydropyrido[3,2-f][1,4]oxazepine hydrochloride

To a solution of cyclobutanol (0.14 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd₂(dba)₃ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give a yellow oil.

A mixture of the obtained oil and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.21 g, 46%) as a white powder.

¹H-NMR (DMSO-d₆): δ1.57-1.60 (2H, m), 1.95-2.05 (2H, m), 2.30-2.40 (2H, m), 3.44 (2H, brs), 4.23-4.33 (4H, m), 5.02 (1H, t, J=7.4 Hz), 6.56 (1H, d, J=8.1 Hz), 7.77 (1H, d, J=8.1 Hz), 9.55 (2H, brs)
MS (ESI+): 221 (M−HCl+H)

Example 9

8-(cyclopentyloxy)-2,3,4,5-tetrahydropyrido[3,2-f][1,4]oxazepine hydrochloride

To a solution of cyclopentanol (0.16 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd₂(dba)₃ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→440% ethyl acetate/hexane) to give a yellow oil.

A mixture of the obtained oil and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.22 g, 48%) as a white powder.

¹H-NMR (DMSO-d₆): δ1.50-1.75 (6H, m), 1.85-1.95 (2H, m), 3.47 (2H, brs), 4.24-4.33 (4H, m), 5.20-5.30 (1H, m), 6.56 (1H, d, J=8.2 Hz), 7.76 (1H, d, J=8.2 Hz), 9.32-9.55 (2H, m)
MS (ESI+): 235 (M−HCl+H)

Example 10

8-(cyclohexyloxy)-2,3,4,5-tetrahydropyrido[3,2-f][1,4]oxazepine hydrochloride (Step 1)
To a solution of cyclohexanol (0.19 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd₂(dba)₃ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(cyclohexyloxy)-2,3-dihydropyrido[3,2-f][1,4]oxazepine-4(5H)-carboxylate (0.40 g, 65%) as a colorless oil.

¹H-NMR (CDCl₃): δ1.20-1.70 (6H, d, J=6.2 Hz), 1.42 (9H, s), 1.70-1.80 (2H, m), 1.90-2.05 (2H, m), 3.76-3.86 (2H, m), 4.21 (2H, brs), 4.33-4.43 (2H, m), 5.01 (1H, brs), 6.39 (1H, d, J=8.0 Hz), 7.30-7.50 (1H, m)

(Step 2)
A mixture of the compound obtained in step 1 (0.40 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.25 g, 50%) as a white powder.

¹H-NMR (DMSO-d₆): δ1.20-1.40 (6H, d, J=6.2 Hz), 1.70-1.80 (2H, m), 1.90-2.05 (2H, m), 3.45 (2H, brs), 4.15-4.35 (4H, m), 4.82-4.92 (1H, m), 6.56 (1H, d, J=8.1 Hz), 7.76 (1H, d, J=8.1 Hz), 9.42 (2H, brs)
MS (ESI+): 249 (M−HCl+H)

Example 11

8-[(2,6-dimethylcyclohexyl)oxy]-2,3,4,5-tetrahydropyrido[3,2-f][1,4]oxazepine hydrochloride (Step 1)
To a solution of 2,6-dimethylcyclohexanol (0.23 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd₂(dba)₃ (0.024 g) and toluene (4 mL) was added, and the resulting mixture was stirred at 100°

C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-[(2,6-dimethylcyclohexyl)oxy]-2,3-dihydropyrido[3,2-f][1,4]oxazepine-4(5H)-carboxylate (0.51 g, 77%) as a colorless oil.

$^1$H-NMR (CDCl$_3$): δ0.75-1.10 (6H, m), 1.15-1.75 (8H, m), 1.43 (9H, s), 3.76-3.86 (2H, m), 4.20 (2H, brs), 4.33-4.50 (2H, m), 4.75&5.44 (total 1H, brs), 6.39-6.44 (1H, m), 7.30-7.50 (1H, m)

(Step 2)

A mixture of the compound obtained in step 1 (0.51 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized from ethanol-diisopropyl ether to give the title compound (0.22 g, 51%) as a white powder.

$^1$H-NMR (DMSO-d$_6$): δ0.71-0.93 (6H, m), 1.29-1.39 (4H, m), 1.50-1.75 (4H, m), 3.37-3.47 (2H, m), 4.25-4.40 (4H, m), 4.65&5.34 (total 1H, m), 6.60&6.62 (total 1H, d, J=8.1 Hz, 8.1 Hz), 7.74&7.75 (total 1H, d, J=8.1 Hz, 6.1 Hz), 9.25 (2H, brs)

MS (ESI+): 277 (M−HCl+H)

Example 12

8-[(2-methylcyclohexyl)oxy]-2,3,4,5-tetrahydropyrido[3,2-f][1,4]oxazepine hydrochloride (Step 1)

To a solution of 2-methylcyclohexanol (0.20 g) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-[(2-methylcyclohexyl)oxy]-2,3-dihydropyrido[3,2-f][1,4]oxazepine-4(5H)-carboxylate (0.55 g, 86%) as a yellow oil.

$^1$H-NMR (CDCl$_3$): δ0.91-0.95 (3H, m), 1.11-1.64 (8H, m), 1.75-1.80&2.05-2.20 (total 1H, m), 1.43 (9H, s), 3.79-3.82 (2H, m), 4.21 (2H, brs), 4.33-4.40 (2H, m), 4.69&5.13 (total 1H, brs), 6.38-6.44 (1H, m), 7.30-7.50 (1H, m)

(Step 2)

A mixture of the compound obtained in step 1 (0.55 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ ethyl acetate was added. The precipitate was collected by filtration, and recrystallized from ethanol-diisopropyl ether to give the title compound (0.38 g, 85%) as a white powder.

$^1$H-NMR (DMSO-d$_6$): δ0.86-0.89 (3H, m), 1.03-2.04 (9H, m), 3.45 (2H, brs), 4.22 (2H, brs), 4.33 (2H, brs), 4.52-4.60&5.01 (total 1H, m), 6.54-6.59 (1H, m), 7.76 (1H, d, J=8.3 Hz), 9.82 (2H, brs)

MS (ESI+): 263 (M−HCl+H)

Example 13

8-ethoxy-2,3,4,5-tetrahydropyrido[3,2-f][1,4]oxazepine hydrochloride (Step 1)

To a solution of ethanol (0.10 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-ethoxy-2,3-dihydropyrido[3,2-f][1,4]oxazepine-4(5H)-carboxylate (0.16 g, 30%) as a colorless oil.

$^1$H-NMR (CDCl$_3$): δ1.36 (3H, t, J=7.2 Hz), 1.42 (9H, s), 3.80-3.83 (2H, m), 4.32 (2H, q, J=7.2 Hz), 4.15-4.43 (4H, m), 6.43 (1H, d, J=8.1 Hz), 7.40-7.52 (1H, m)

(Step 2)

A mixture of the compound obtained in step 1 (0.16 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ ethyl acetate was added. The precipitate was collected by filtration, and recrystallized from ethanol-diisopropyl ether to give the title compound (0.10 g, 78%) as a white powder.

$^1$H-NMR (DMSO-d$_6$): δ1.29 (3H, t, J=7.0 Hz), 3.40-3.47 (2H, m), 4.20-4.24 (4H, m), 4.31-4.34 (2H, m), 6.59 (1H, d, J=8.1 Hz), 7.78 (1H, d, J=8.1 Hz), 9.60 (2H, brs)

MS (ESI+): 195 (M−HCl+H)

Example 14

8-[(trans-2-methylcyclopentyl)oxy]-2,3,4,5-tetrahydropyrido[3,2-f][1,4]oxazepine dihydrochloride (Step 1)

To a solution of trans-2-methylcyclopentanol (0.18 g) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-[(trans-2-methylcyclopentyl)oxy]-2,3-dihydropyrido[3,2-f][1,4]oxazepine-4(5H)-carboxylate (0.46 g, 75%) as a colorless oil.

$^1$H-NMR (CDCl$_3$): δ1.04 (3H, d, J=6.7 Hz), 1.20-1.30 (1H, m), 1.42 (9H, s), 1.55-1.80 (3H, m), 1.89-2.00 (1H, m), 2.04-2.17 (2H, m), 3.81 (2H, brs), 4.21 (2H, brs), 4.34-4.43 (2H, m), 4.90 (1H, brs), 6.39 (1H, d, J=8.0 Hz), 7.37-7.50 (1H, m)
(Step 2)

A mixture of the compound obtained in step 1 (0.46 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.18 g, 44%) as a white powder.

$^1$H-NMR (DMSO-d$_6$): δ1.01 (3H, d, J=7.0 Hz), 1.14-1.26 (1H, m), 1.48-1.60 (1H, m), 1.60-1.71 (2H, m), 1.83-1.95 (1H, m), 1.95-2.12 (2H, m), 3.45 (2H, brs), 4.23 (2H, brs), 4.33 (2H, brs), 4.77-4.82 (1H, m), 6.56 (1H, d, J=8.2 Hz), 7.77 (1H, d, J=8.2 Hz), 9.81 (2H, brs)
MS (ESI+): 249 (M−HCl+H)

Example 15

8-(1-cyclopropylethoxy)-2,3,4,5-tetrahydropyrido[3,2-f][1,4]oxazepine (Step 1)
To a solution of 1-cyclopropylethanol (0.17 mL) in toluene (4 mL) was added sodium hydride (0.14 g), and the resulting mixture was stirred at 70° C. for 15 min under a nitrogen atmosphere. A mixture of 4-benzyl-8-chloro-2,3,4,5-tetrahydropyrido[3,2-f][1,4]oxazepine (0.48 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-(1-cyclopropylethoxy)-2,3,4,5-tetrahydropyrido[3,2-f][1,4]oxazepine (0.42 g, 74%) as a yellow oil.

$^1$H-NMR (CDCl$_3$): δ0.27-0.33 (1H, m), 0.38-0.45 (1H, m), 0.48-0.55 (2H, m), 1.05-1.20 (1H, m), 1.37 (3H, d, J=6.2 Hz), 3.04-3.07 (2H, m), 3.65 (2H, s), 3.66 (2H, s), 4.18-4.21 (2H, m), 4.55-4.70 (1H, m), 6.40 (1H, d, J=8.0 Hz), 7.24 (1H, d, J=8.0 Hz), 7.20-7.35 (5H, m)
(Step 2)

A mixture of the compound obtained in step 1 (0.15 g), 20% Pd(OH)$_2$/C (0.020 g) and methanol (3 mL) was stirred at 50° C. for 15 hr under a hydrogen atmosphere. The insoluble material was removed by filtration, and the filtrate was concentrated under reduced pressure. The residue was purified by basic silica gel column chromatography (solvent gradient; 0→40% ethyl acetate/hexane) to give the title compound (0.11 g, quantitatively) as a colorless oil.

$^1$H-NMR (CDCl$_3$): δ0.25-0.35 (1H, m), 0.35-0.45 (1H, m), 0.45-0.60 (2H, m), 1.00-1.20 (1H, m), 1.36 (3H, d, J=6.2 Hz), 1.76-1.86 (1H, m), 3.21-3.24 (2H, m), 3.86 (2H, s), 4.17-4.20 (2H, m), 4.57-4.70 (1H, m), 6.40 (1H, d, J=8.0 Hz), 7.36 (1H, d, J=8.0 Hz) MS (ESI+): 235 (M+H)

Example 16

8-(1-cyclopropylethoxy)-2,3,4,5-tetrahydropyrido[3,2-f][1,4]oxazepine 0.5 succinate To the compound obtained in Example 15 (0.11 g) was added 0.5 M succinic acid/methanol solution (0.47 mL), and the solvent was evaporated under reduced pressure. The obtained residue was recrystallized from ethyl acetate-hexane to give the title compound (0.042 g, 30%) as a white powder.

$^1$H-NMR (CDCl$_3$): δ0.29-0.43 (1H, m), 0.47-0.49 (1H, m), 0.50-0.60 (2H, m), 1.00-1.20 (1H, m), 1.36 (3H, d, J=6.2 Hz), 2.47 (2H, s), 3.34-3.37 (2H, m), 4.00 (2H, s), 4.24-4.27 (2H, m), 4.55-4.65 (1H, m), 4.20 (2H, brs), 6.44 (1H, d, J=8.0 Hz), 7.43 (1H, d, J=8.0 Hz)
MS (ESI+): 235 (M−0.5C$_4$H$_6$C$_4$+H)

Example 17

8-butoxy-2,3,4,5-tetrahydropyrido[3,2-f][1,4]oxazepine hydrochloride (Step 1)
A solution of 1-butanol (0.16 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-butoxy-2,3-dihydropyrido[3,2-f][1,4]oxazepine-4(5H)-carboxylate (0.40 g, 70%) as a yellow oil.

$^1$H-NMR (CDCl$_3$): δ0.96 (3H, t, J=7.4 Hz), 1.42 (9H, s), 1.40-1.55 (2H, m), 1.68-1.80 (2H, m), 3.80-3.83 (2H, m), 4.20-4.30 (4H, m), 4.34-4.43 (2H, m), 6.43 (1H, d, J=7.9 Hz), 7.39-7.55 (1H, m)
(Step 2)

A mixture of the compound obtained in step 1 (0.36 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.24 g, 84%) as a white powder.

$^1$H-NMR (DMSO-d$_6$): δ0.91 (3H, t, J=7.4 Hz), 1.30-1.45 (2H, m), 1.61-1.70 (2H, m), 3.47 (2H, brs), 4.18 (2H, t, J=6.6 Hz), 4.25 (2H, s), 4.30-4.35 (2H, m), 6.59 (1H, d, J=8.1 Hz), 7.78 (1H, d, J=8.1 Hz), 9.55 (2H, brs)
MS (ESI+): 223 (M−HCl+H)

Example 18

8-(benzyloxy)-2,3,4,5-tetrahydropyrido[3,2-f][1,4]oxazepine hydrochloride (Step 1)

To a solution of benzyl alcohol (0.18 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(benzyloxy)-2,3-dihydropyrido[3,2-f][1,4]oxazepine-4(5H)-carboxylate (0.44 g, 71%) as a yellow oil.

$^1$H-NMR (CDCl$_3$): δ1.42 (9H, s), 3.82-3.84 (2H, m), 4.24 (2H, brs), 4.36-4.45 (2H, m), 5.33 (2H, s), 6.52 (1H, d, J=7.9 Hz), 7.27-7.60 (6H, m)

(Step 2)

A mixture of the compound obtained in step 1 (0.40 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.28 g, 83%) as a white powder.

$^1$H-NMR (DMSO-d$_6$): δ3.49 (2H, brs), 4.27 (2H, s), 4.33-4.36 (2H, m), 5.29 (2H, s), 6.68 (1H, d, J=8.2 Hz), 7.32-7.45 (5H, m), 7.82 (1H, d, J=8.2 Hz), 9.54 (2H, brs)

MS (ESI+): 257 (M−HCl+H)

Example 19

8-propoxy-2,3,4,5-tetrahydropyrido[3,2-f][1,4]oxazepine hydrochloride (Step 1)

To a solution of 1-propanol (0.13 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-propoxy-2,3-dihydropyrido[3,2-f][1,4]oxazepine-4(5H)-carboxylate (0.38 g, 71%) as a yellow oil.

$^1$H-NMR (CDCl$_3$): δ1.00 (3H, t, J=7.5 Hz), 1.42 (9H, s), 1.71-1.83 (2H, m), 3.80-3.83 (2H, m), 4.19-4.23 (4H, m), 4.34-4.50 (2H, m), 6.44 (1H, d, J=7.9 Hz), 7.40-7.55 (1H, m)

(Step 2)

A mixture of the compound obtained in step 1 (0.36 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.25 g, 87%) as a white powder.

$^1$H-NMR (DMSO-d$_6$): δ0.94 (3H, t, J=7.4 Hz), 1.60-1.75 (2H, m), 3.45 (2H, brs), 4.13 (2H, t, J=6.7 Hz), 4.25 (2H, brs), 4.30-4.33 (2H, m), 6.60 (1H, d, J=8.1 Hz), 7.78 (1H, d, J=8.1 Hz), 9.54 (2H, brs)

MS (ESI+): 209 (M−HCl+H)

Example 20

8-(1,2,2-trimethylpropoxy)-2,3,4,5-tetrahydropyrido[3,2-f][1,4]oxazepine hydrochloride (Step 1)

To a solution of 3,3-dimethylbutan-2-ol (0.18 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(1,2,2-trimethylpropoxy)-2,3-dihydropyrido[3,2-f][1,4]oxazepine-4(5H)-carboxylate (0.38 g, 62%) as a white powder.

$^1$H-NMR (CDCl$_3$): δ0.95 (9H, s), 1.20 (3H, d, J=6.4 Hz), 1.43 (9H, s), 3.80-3.83 (2H, m), 4.22 (2H, brs), 4.34-4.50 (2H, m), 4.91 (1H, brs), 6.39 (1H, d, J=8.1 Hz), 7.30-7.55 (1H, m)

(Step 2)

A mixture of the compound obtained in step 1 (0.15 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.11 g, 93%) as a white powder.

$^1$H-NMR (DMSO-d$_6$): δ0.92 (9H, s), 1.14 (3H, d, J=6.4 Hz), 3.47 (2H, brs), 4.24 (2H, brs), 4.32-4.33 (2H, m), 4.82 (1H, q, J=6.4 Hz), 6.56 (1H, d, J=8.1 Hz), 7.75 (1H, d, J=8.1 Hz), 9.51 (2H, brs)

MS (ESI+): 251 (M−HCl+H)

Example 21

8-(1,2-dimethylbutoxy)-2,3,4,5-tetrahydropyrido[3,2-f][1,4]oxazepine hydrochloride (Step 1)

To a solution of 3-methylpentan-2-ol (0.18 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(1,2-dimethylbutoxy)-2,3-dihydropyrido[3,2-f][1,4]oxazepine-4(5H)-carboxylate (0.37 g, 61%) as a yellow oil.

$^1$H-NMR (CDCl$_3$): δ0.86-0.96 (6H, m), 1.10-1.30 (5H, m), 1.43 (9H, s), 1.50-1.60 (1H, m), 3.79-3.82 (2H, m), 4.21 (2H, brs), 4.34-4.43 (2H, m), 5.06 (1H, brs), 6.39 (1H, d, J=7.9 Hz), 7.39-7.50 (1H, m)

(Step 2)

A mixture of the compound obtained in step 1 (0.10 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.055 g, 67%) as a white powder.

$^1$H-NMR (DMSO-d$_6$): 0.84-0.92 (6H, m), 1.15-1.19 (4H, m), 1.40-1.75 (2H, m), 3.48 (2H, brs), 4.25 (2H, s), 4.31-4.34 (2H, m), 4.90-5.10 (1H, m), 6.54-6.57 (1H, m), 7.75 (1H, d, J=8.1 Hz), 9.34 (2H, brs)

MS (ESI+): 251 (M−HCl+H)

Example 22

8-sec-butoxy-2,3,4,5-tetrahydropyrido[3,2-f][1,4]oxazepine hydrochloride (Step 1)

To a solution of sec-butanol (0.16 mL) in toluene (4 mL) was added sodium hydride (0.14 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), Pd$_2$(dba)$_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl B-sec-butoxy-2,3-dihydropyrido[3,2-f][1,4]oxazepine-4(5H)-carboxylate (0.34 g, 60%) as a yellow oil.

$^1$H-NMR (CDCl$_3$): δ0.94 (3H=7.4 Hz), 1.28 (3H, d, J=6.3 Hz), 1.43 (9H, s), 1.63-1.75 (2H, m), 3.76-3.86 (2H, m), 4.21 (2H, brs), 4.34-4.43 (2H, m), 5.10 (1H, brs), 6.39 (1H, d, J=8.1 Hz), 7.38-7.47 (1H, m)

(Step 2)

A mixture of the compound obtained in step 1 (0.34 g) and 4N hydrogen chloride/ethyl acetate (3 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.22 g, 82%) as a white powder.

$^1$H-NMR (DMSO-d$_6$): δ0.88 (3H, t, J=7.5 Hz), 1.22 (3H, d, J=6.3 Hz), 1.55-1.66 (2H, m), 3.34-3.45 (2H, m), 4.24 (2H, brs), 4.26-4.36 (2H, m), 4.92-5.02 (1H, m), 6.55 (1H, d, J=8.1 Hz), 7.76 (1H, d, J=8.1 Hz), 9.48 (2H, brs)

MS (ESI+): 223 (M−HCl+H)

Example 23

8-[(4,4-difluorocyclohexyl)oxy]-2,3,4,5-tetrahydropyrido[3,2-f][1,4]oxazepine hydrochloride (Step 1)

To a solution of 4,4-difluorocyclohexanone (0.25 g) in methanol (10 mL) was added sodium borohydride (0.085 g) at 0° C., and the resulting mixture was stirred at room temperature for 16 hr. The reaction solution was poured into water, and the resulting product was extracted with ethyl acetate. The organic layer was washed with water and saturated brine and dried, and the solvent was evaporated under reduced pressure. To a solution of the obtained residue in toluene (5 mL) was added sodium hydride (0.15 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.035 g), Pd$_2$(dba)$_3$ (0.026 g) and toluene (5 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-[(4,4-difluorocyclohexyl)oxy]-2,3-dihydropyrido[3,2-f][1,4]oxazepine-4(5H)-carboxylate (0.27 g, 38%) as a white powder.

$^1$H-NMR (CDCl$_3$): δ1.42 (9H, s), 1.85-2.25 (8H, m), 3.80-3.83 (2H, m), 4.22 (2H, brs), 4.35-4.50 (2H, m), 5.22 (1H, brs), 6.43 (1H, d, J=7.9 Hz), 7.41-7.52 (1H, m)

(Step 2)

A mixture of the compound obtained in step 1 (0.23 g) and 4N hydrogen chloride/ethyl acetate (5 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.16 g, 82%) as a white powder.

$^1$H-NMR (DMSO-d$_6$): δ1.70-1.85 (2H, m), 1.85-2.20 (6H, m), 3.46-3.48 (2H, m), 4.25 (2H, s), 4.30-4.33 (2H, m), 5.09 (1H, brs), 6.62 (1H, d, J=8.2 Hz), 7.79 (1H, d, J=8.2 Hz), 9.39 (2H, brs)

Example 24

8-{[(1S)-1,2-dimethylpropyl]oxy}-2,3,4,5-tetrahydropyrido[3,2-f][1,4]oxazepine hydrochloride (Step 1)
To a solution of (2S)-3-methylbutan-2-ol (0.38 mL) in toluene (8 mL) was added sodium hydride (0.28 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (1.0 g), BINAP (0.066 g), Pd$_2$(dba)$_3$ (0.048 g) and toluene (8 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-{[(1S)-1,2-dimethylpropyl]oxy}-2,3-dihydropyrido[3,2-f][1,4]oxazepine-4(5H)-carboxylate (0.79 g, 67%) as a white powder.

$^1$H-NMR (CDCl$_3$): δ0.94 (3H, d, J=6.8 Hz), 0.96 (3H, d, J=6.6 Hz), 1.23 (3H, d, J=6.2 Hz), 1.43 (9H, s), 1.82-1.95 (1H, m), 3.75-3.85 (2H, m), 4.21 (2H, brs), 4.34-4.43 (2H, m), 4.97 (1H, brs), 6.39 (1H, d, J=7.9 Hz), 7.30-7.50 (1H, m)
(Step 2)
A mixture of the compound obtained in step 1 (0.79 g) and 4N hydrogen chloride/ethyl acetate (10 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized twice from ethanol-diisopropyl ether to give the title compound (0.48 g, 75%) as a white powder.

$^1$H-NMR (DMSO-d$_6$): δ0.90 (3H, d, J=6.8 Hz), 0.91 (3H, d, J=6.8 Hz) 1.17 (3H, d, J=6.2 Hz), 1.81-1.91 (1H, m), 3.45 (2H, brs), 4.20-4.40 (4H, m), 4.81-4.91 (1H, m), 6.55 (1H, d, J=8.1 Hz), 7.76 (1H, d, J=8.1 Hz), 9.75 (2H, brs)
MS (ESI+): 237 (M−HCl+H)
[α]$_D^{25}$+22.6 (c 1.0, MeOH)

Example 25

8-{[(1R)-1,2-dimethylpropyl]oxy}-2,3,4,5-tetrahydropyrido[3,2-f][1,4]oxazepine hydrochloride (Step 1)
To a solution of (2R)-3-methylbutan-2-ol (0.38 mL) in toluene (8 mL) was added sodium hydride (0.28 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (1.0 g), BINAP (0.066 g), Pd$_2$(dba)$_3$ (0.048 g) and toluene (8 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-{[(1R)-1,2-dimethylpropyl]oxy}-2,3-dihydropyrido[3,2-f][1,4]oxazepine-4(5H)-carboxylate (0.77 g, 65%) as a white powder.

$^1$H-NMR (CDCl$_3$): δ0.94 (3H, d, J=6.8 Hz), 0.96 (3H, d, J=6.6 Hz), 1.23 (3H, d, J=6.2 Hz), 1.43 (9H, s), 1.82-1.95 (1H, m), 3.81 (2H, brs), 4.21 (2H, brs), 4.34-4.43 (2H, m), 4.97 (1H, brs), 6.40 (1H, brs), 7.30-7.50 (1H, m)
(Step 2)
A mixture of the compound obtained in step 1 (0.77 g) and 4N hydrogen chloride/ethyl acetate (10 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration and recrystallized twice from ethanol-diisopropyl ether to give the title compound (0.48 g, 78%) as a white powder.

$^1$H-NMR (DMSO-d$_6$): δ0.90 (3H, d, J=6.8 Hz), 0.91 (3H, d, J=6.8 Hz), 1.17 (3H, d, J=6.2 Hz), 1.81-1.91 (1H, m), 3.45 (2H, brs), 4.20-4.40 (4H, m), 4.81-4.91 (1H, m), 6.55 (1H, d, J=8.1 Hz), 7.76 (1H, d, J=8.1 Hz), 9.82 (2H, brs)
MS (ESI+): 237 (M−HCl+H)
[α]$_D^{25}$-22.7 (c 1.0, MeOH)

Example 26

8-{[(1S)-1-methylpropyl]oxy}-2,3,4,5-tetrahydropyrido[3,2-f][1,4]oxazepine hydrochloride (Step 1)
To a solution of (2S)-butan-2-ol (0.32 mL) in toluene (8 mL) was added sodium hydride (0.28 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (1.0 g), BINAP (0.066 g), Pd$_2$(dba)$_3$ (0.048 g) and toluene (8 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-{[(1S)-1-methylpropyl]oxy}-2,3-dihydropyrido[3,2-f][1,4]oxazepine-4(5H)-carboxylate (0.73 g, 65%) as a white powder.

$^1$H-NMR (CDCl$_3$): δ0.94 (3H, t, J=7.4 Hz), 1.27 (3H, d, J=6.3 Hz) 1.42 (9H, s), 1.63-1.75 (2H, m), 3.76-3.86 (2H, m), 4.21 (2H, brs), 4.34-4.43 (2H, m), 5.10 (1H, brs), 6.39 (1H, d, J=8.1 Hz), 7.38-7.47 (1H, m)
(Step 2)
A mixture of the compound obtained in step 1 (0.70 g) and 4N hydrogen chloride/ethyl acetate (5 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.40 g, 70%) as a white powder.

$^1$H-NMR (DMSO-d$_6$): δ0.88 (3H, t, J=7.5 Hz), 1.22 (3H, d, J=6.3 Hz), 1.55-1.66 (2H, m), 3.45-3.50 (2H, m), 4.25 (2H, brs), 4.26-4.36 (2H, m), 4.92-5.02 (1H, m), 6.56 (1H, d, J=8.1 Hz), 7.75 (1H, d, J=8.1 Hz), 9.33 (2H, brs)

MS (ESI+): 223 (M−HCl+H)

[α]$_D^{25}$+25.4 (c 1.0, MeOH)

Example 27

8-{[(1R)-1-methylpropyl]oxy}-2,3,4,5-tetrahydropyrido[3,2-f][1,4]oxazepine hydrochloride (Step 1)

To a solution of (2R)-butan-2-ol (0.32 mL) in toluene (8 mL) was added sodium hydride (0.28 g), and the resulting mixture was stirred at 70° C. for 15 min under a nitrogen atmosphere. A mixture of tert-butyl 8-chloro-2,3-dihydropyrido[3,2-f][1,4]oxazepine-4(5H)-carboxylate (1.0 g), BINAP (0.066 g), Pd$_2$(dba)$_3$ (0.048 g) and toluene (8 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-{[(1R)-1-methylpropyl]oxy}-2,3-dihydropyrido[3,2-f][1,4]oxazepine-4(5H)-carboxylate (0.79 g, 70%) as a white powder.

$^1$H-NMR (CDCl$_3$): δ0.94 (3H, t, J=7.4 Hz), 1.27 (3H, d, J=6.3 Hz), 1.42 (9H, s), 1.63-1.75 (2H, m), 3.79-3.83 (2H, m), 4.21 (2H, brs), 4.34-4.43 (2H, m), 5.10 (1H, brs), 6.39 (1H, d, J=8.1 Hz), 7.38-7.47 (1H, m)

(Step 2)

A mixture of the compound obtained in step 1 (0.70 g) and 4N hydrogen chloride/ethyl acetate (5 mL) was stirred at room temperature for 3 hr. The precipitate was collected by filtration, and the aqueous layer was basified and extracted with ethyl acetate and aqueous sodium hydroxide solution. The organic layer was washed with saturated brine and dried, and the solvent was evaporated under reduced pressure. Ethyl acetate was added to the residue, and 4N hydrogen chloride/ethyl acetate was added. The precipitate was collected by filtration, and recrystallized from ethanol-diisopropyl ether to give the title compound (0.36 g, 60%) as a white powder.

$^1$H-NMR (DMSO-d$_6$): δ0.88 (3H, t, J=7.5 Hz), 1.22 (3H, d, J=6.3 Hz), 1.55-1.66 (2H, m), 3.47 (2H, brs), 4.24 (2H, brs), 4.26-4.36 (2H, m), 4.94-5.00 (1H, m), 6.56 (1H, d, J=8.1 Hz), 7.75 (1H, d, J=8.1 Hz), 9.51 (2H, brs)

MS (ESI+): 223 (M−HCl+H)

[α]$_D^{25}$−27.5 (c 1.0, MeOH)

Example 28

8-phenoxy-2,3,4,5-tetrahydropyrido[3,2-f][1,4]oxazepine hydrochloride (Step 1)

To a mixture of 2,6-difluoronicotinic acid (20.0 g), DMF (4 mL) and toluene (400 mL) was added oxalyl dichloride (11.9 mL) at 0° C. The mixture was stirred at room temperature for 1 hr, and the solvent was evaporated under reduced pressure. THF (120 mL) was added to the residue, and a solution of N-benzylethanolamine (20.9 g) in THF was added. 8M Aqueous sodium hydroxide solution (40 mL) was added at 0° C., and the resulting mixture was stirred at room temperature for 16 hr. Ethyl acetate and water were added, and the organic layer was washed with water and saturated brine and dried, and the solvent was evaporated under reduced pressure. THF (100 mL) was added to the obtained residue (34.5 g), and a suspension of sodium hydride (5.70 g) in THF (400 mL) was added dropwise at 0° C. The mixture was stirred at room temperature for 16 hr, and water was added. The resulting product was extracted with ethyl acetate, the organic layer was washed with water and saturated brine and dried, and the solvent was evaporated under reduced pressure. The residue was purified by silica gel column chromatography (solvent gradient; 50→100% ethyl acetate/hexane) to give 4-benzyl-8-fluoro-3,4-dihydropyrido[3,2-f][1,4]oxazepin-5(2H)-one (11.2 g, 33%) as a yellow oil.

$^1$H-NMR (CDCl$_3$): δ3.61-3.64 (2H, m), 4.38-4.41 (2H, m), 4.82 (2H, s), 6.74 (1H, =3.4, 8.3 Hz), 7.20-7.40 (5H, m), 8.67 (1H, t, J=8.3 Hz)

(Step 2)

A mixture of the compound obtained in step 1 (0.50 g), phenol (0.21 g), potassium carbonate (0.76 g) and DMF (5 mL) was stirred at 100° C. for 3 days. The reaction solution was poured into water, and the resulting product was extracted with ethyl acetate. The organic layer was washed with water and saturated brine and dried, and the solvent was evaporated under reduced pressure. The residue was recrystallized from ethyl acetate-hexane to give 4-benzyl-8-phenoxy-3,4-dihydropyrido[3,2-f][1,4]oxazepin-5(2H)-one (0.42 g, 66%) as a white powder.

$^1$H-NMR (CDCl$_3$): δ3.57-3.60 (2H, m), 4.31-4.34 (2H, m), 4.81 (2H, s), 6.67 (1H, d, J=8.6 Hz), 7.13-7.45 (10H, m), 8.59 (1H, t, J=8.6 Hz)

(Step 3)

To a mixture of lithium aluminum hydride (0.066 g) and THF-diethyl ether (2 mL-10 mL) was added the compound obtained in step 2 (0.40 g), and the resulting mixture was stirred at room temperature for 3 hr under a nitrogen atmosphere. Lithium aluminum hydride (0.066 g) was added again, and the resulting mixture was stirred at room temperature for 2 hr under a nitrogen atmosphere. 1N Aqueous sodium hydroxide solution (0.13 mL), saturated aqueous ammonium chloride (0.13 mL) and water (0.13 mL) were added, and the resulting mixture was stirred at room temperature for 4 hr. The precipitate was removed by filtration, and the filtrate was concentrated under reduced pressure. The residue was purified by silica gel column chromatography (solvent gradient; 0→40% ethyl acetate/hexane) to give 4-benzyl-8-phenoxy-2,3,4,5-tetrahydropyrido[3,2-f][1,4]oxazepine (0.19 g, 50%) as a white powder.

$^1$H-NMR (CDCl$_3$): δ3.05-3.08 (2H, m), 3.68 (2H, s), 3.70 (2H, s), 4.18-4.21 (2H, m), 6.50 (1H, d, J=7.9 Hz), 7.10-7.40 (11H, m)

(Step 4)

A mixture of the compound obtained in step 3 (0.17 g), 20% Pd(OH)$_2$/C (0.020 g) and methanol (5 mL) was stirred at room temperature for 3 hr under a hydrogen atmosphere. The insoluble material was removed by filtration, and the filtrate was concentrated under reduced pressure. The residue was dissolved in ethyl acetate, and 4N hydrogen chloride/ethyl acetate was added. The solvent was evaporated under reduced pressure, and the residue was recrystallized from methanol-ethanol-diisopropyl ether to give the title compound (0.093 g, 65%) as a white powder.

$^1$H-NMR (DMSO-d$_6$): δ3.34-3.47 (2H, m), 4.25-4.35 (4H, m), 6.79 (1H, d, J=8.1 Hz), 7.12 (2H, d, J=7.7 Hz), 7.20-7.27 (1H, m), 7.41-7.46 (2H, m), 7.94 (1H, d, J=8.1 Hz), 9.70 (2H, brs)

MS (ESI+): 243 (M−HCl+H)

Example 29

8-(1-cyclopentylethoxy)-2,3,4,5-tetrahydropyrido[3,2-f][1,4]oxazepine hydrochloride (Step 1)

To a solution of 1-cyclopentylethanol (0.22 mL) in toluene (4 mL) was added sodium hydride (0.14 g), and the resulting mixture was stirred at 100° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), $Pd_2(dba)_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(1-cyclopentylethoxy)-2,3-dihydropyrido[3,2-f][1,4]oxazepine-4(5H)-carboxylate (0.45 g, 70%) as a white powder.
$^1$H-NMR (CDCl$_3$): δ1.27 (3H, t, J=6.0 Hz), 1.25-1.85 (8H, m), 1.43 (9H, s), 2.00-2.12 (1H, m), 3.80-3.82 (2H, m), 4.21 (2H, brs), 4.33-4.45 (2H, m), 5.01 (1H, brs), 6.38 (1H, d, J=8.1 Hz), 7.30-7.50 (1H, m)

(Step 2)

A mixture of the compound obtained in step 1 (0.42 g) and 4N hydrogen chloride/ethyl acetate (3 mL) was stirred at room temperature for 3 hr. The precipitate was collected by filtration, and recrystallized from ethanol-diisopropyl ether to give the title compound (0.24 g, 71%) as a white powder.
$^1$H-NMR (DMSO-d$_6$): δ1.22 (3H, t, J=8.1 Hz), 1.20-1.40 (2H, m), 1.48-1.65 (4H, m), 1.65-1.80 (2H, m), 2.00-2.35 (1H, m), 3.46 (2H, brs), 4.23-4.34 (4H, m), 4.85-5.00 (1H, m), 6.54 (1H, d, J=8.2 Hz), 7.75 (1H, d, J=8.2 Hz), 9.59 (2H, brs)
MS (ESI+): 263 (M−HCl+H)

Example 30

8-(1-cyclohexylethoxy)-2,3,4,5-tetrahydropyrido[3,2-f][1,4]oxazepine hydrochloride (Step 1)

To a solution of 1-cyclohexylethanol (0.23 g) in toluene (4 mL) was added sodium hydride (0.14 g), and the resulting mixture was stirred at 100° C. for 15 min under a nitrogen atmosphere. A mixture of tert-butyl 8-chloro-2,3-dihydropyrido[3,2-f][1,4]oxazepine-4(5H)-carboxylate (0.50 g), BINAP (0.033 g), $Pd_2(dba)_3$ (0.024 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give tert-butyl 8-(1-cyclohexylethoxy)-2,3-dihydropyrido[3,2-f][1,4]oxazepine-4(5H)-carboxylate (0.49 g, 74%) as a yellow oil.
$^1$H-NMR (CDCl$_3$): δ1.23 (3H, t, J=6.2 Hz), 1.03-1.40 (6H, m), 1.42 (9H, s), 1.42-1.95 (5H, m), 3.79-3.82 (2H, m), 4.20 (2H, brs), 4.33-4.45 (2H, m), 4.97 (1H, brs), 6.38 (1H, d, J=7.9 Hz), 7.30-7.50 (1H, m)

(Step 2)

A mixture of the compound obtained in step 1 (0.47 g) and 4N hydrogen chloride/ethyl acetate (3 mL) was stirred at room temperature for 3 hr. The precipitate was collected by filtration, and recrystallized from ethanol-diisopropyl ether to give the title compound (0.31 g, 79%) as a white powder.
$^1$H-NMR (DMSO-d$_6$): δ0.85-1.30 (5H, m), 1.18 (3H, t, J=6.2 Hz), 1.45-1.85 (6H, m), 3.56 (2H, brs), 4.24-4.32 (4H, m), 4.84-5.00 (1H, m), 6.55 (1H, d, J=8.1 Hz), 7.75 (1H, d, J=8.1 Hz), 9.56 (2H, brs)
MS (ESI+): 277 (M−HCl+H)

Example 31

8-(dicyclopropylmethoxy)-2,3,4,5-tetrahydropyrido[3,2-f][1,4]oxazepine 0.5 succinate (Step 1)

To a solution of dicyclopropylmethanol (0.20 g) in toluene (4 mL) was added sodium hydride (0.15 g), and the resulting mixture was stirred at 100° C. for 15 min under a nitrogen atmosphere. A mixture of 4-benzyl-8-chloro-2,3,4,5-tetrahydropyrido[3,2-f][1,4]oxazepine (0.50 g), BINAP (0.034 g), $Pd_2(dba)_3$ (0.025 g) and toluene (4 mL) was added, and the resulting mixture was stirred at 100° C. for 2 hr under an argon atmosphere. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-(1-dicyclopropylmethoxy)-2,3,4,5-tetrahydropyrido[3,2-f][1,4]oxazepine (0.52 g, 82%) as a yellow oil.
$^1$H-NMR (CDCl$_3$): δ0.35-0.65 (8H, m), 1.05-1.20 (2H, m), 3.04-3.07 (2H, m), 3.65 (2H, s), 3.66 (2H, s), 4.17-4.20 (2H, m), 4.43 (1H, dd, J=7.8, 7.8 Hz), 6.42 (1H, d, J=7.9 Hz), 7.23-7.33 (6H, m)

(Step 2)

A mixture of the compound obtained in step 1 (0.50 g), 20% Pd(OH)$_2$/C (0.050 g) and methanol (10 mL) was stirred at 40° C. for 2 hr under a hydrogen atmosphere. The insoluble material was removed by filtration, and the filtrate was concentrated under reduced pressure. To the residue was added 0.5M succinic acid/methanol solution (1.5 mL), and the solvent was evaporated under reduced pressure. The obtained residue was recrystallized from ethyl acetate-hexane to give the title compound (0.097 g, 22%) as a white powder.
$^1$H-NMR (CDCl$_3$): δ0.35-0.60 (8H, m), 1.05-1.20 (2H, m), 2.47 (2H, s), 3.34-3.37 (2H, m), 4.00 (2H, s), 4.23-4.26 (2H, m), 4.40 (1H, dd, J=7.8, 7.8 Hz), 5.67 (2H, brs), 6.45 (1H, d, J=7.9 Hz), 7.43 (1H, d, J=7.9 Hz)

Example 32

8-(2-chlorophenoxy)-2,3,4,5-tetrahydropyrido[3,2-f][1,4]oxazepine hydrochloride (Step 1)

A mixture of the compound obtained in Example 28, step 1 (0.50 g), 2-chlorophenol (0.23 mL), potassium carbonate (0.76 g) and DMF (10 mL) was stirred at 100° C. for 16 hr. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-(2-chlorophenoxy)-3,4-dihydropyrido[3,2-f][1,4]oxazepin-5(2H)-one (0.59 g, 84%) as a colorless oil.

$^1$H-NMR (CDCl$_3$): δ3.57-3.60 (2H, m), 4.29-4.32 (2H, m), 4.80 (2H, s), 6.74 (1H, d, J=8.5 Hz), 7.10-7.40 (8H, m), 7.45 (1H, dd, J=1.6, 7.8 Hz), 8.62 (1H, d, J=8.5 Hz)

(Step 2)

To a mixture of lithium aluminum hydride (0.080 g) and THF-diethyl ether solution (2.5 mL-2.5 mL) was added a solution of the compound obtained in step 1 (0.54 g) in THF-diethyl ether (2.5 mL-2.5 mL), and the resulting mixture was stirred at room temperature for 2 hr under a nitrogen atmosphere. 1N Aqueous sodium hydroxide solution (0.080 mL), saturated aqueous ammonium chloride (0.080 mL) and water (0.080 mL) were added, and the resulting mixture was stirred at room temperature for 3 hr. The precipitate was removed by filtration, and the filtrate was concentrated under reduced pressure. The residue was purified by silica gel column chromatography (solvent gradient; 0→40% ethyl acetate/hexane) to give 4-benzyl-8-(2-chlorophenoxy)-2,3,4,5-tetrahydropyrido[3,2-f][1,4]oxazepine (0.30 g, 58%) as a colorless oil.

$^1$H-NMR (CDCl$_3$): δ3.04-3.06 (2H, m), 3.67 (2H, s), 3.70 (2H, s), 4.16-4.19 (2H, m), 6.57 (1H, d, J=8.0 Hz), 7.11-7.19 (2H, m), 7.24-7.39 (7H, m), 7.44 (1H, d, J=8.0 Hz)

(Step 3)

To a solution of the compound obtained in step 2 (0.28 g) in dichloroethane (3 mL) was added 1-chloroethyl chloroformate (0.074 mL), and the resulting mixture was stirred at 90° C. for 2 hr. The solvent was evaporated under reduced pressure, and methanol (3 mL) was added. The mixture was stirred at 80° C. for 1 hr. Diisopropyl ether (3 mL) was added, and the precipitate was collected by filtration, and recrystallized from ethanol-diisopropyl ether to give the title compound (0.21 g, 89%) as a white powder.

$^1$H-NMR (DMSO-d$_6$): δ3.46 (2H, brs), 4.31 (4H, brs), 6.88 (1H, d, J=8.0 Hz), 7.29-7.34 (2H, m), 7.41-7.46 (1H, m), 7.60 (1H, d, J=7.7 Hz), 7.96 (1H, d, J=8.0 Hz), 9.60-9.90 (2H, m)

MS (ESI+): 277 (M−HCl+H)

Example 33

8-(3-chlorophenoxy)-2,3,4,5-tetrahydropyrido[3,2-f][1,4]oxazepine hydrochloride (Step 1)

A mixture of the compound obtained in Example 28, step 1 (0.50 g), 3-chlorophenol (0.23 mL), potassium carbonate (0.76 g) and DMF (10 mL) was stirred at 100° C. for 16 hr. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-(3-chlorophenoxy)-3,4-dihydropyrido[3,2-f][1,4]oxazepin-5(2H)-one (0.58 g, 83%) as a colorless oil.

$^1$H-NMR (CDCl$_3$): δ3.58-3.61 (2H, m), 4.32-4.34 (2H, m), 4.81 (2H, s), 6.71 (1H, d, J=8.5 Hz), 7.04-7.07 (1H, m), 7.16-7.20 (2H, m), 7.26-7.40 (6H, m), 8.62 (1H, d, J=8.5 Hz)

(Step 2)

To a mixture of lithium aluminum hydride (0.079 g) and THF-diethyl ether solution (2.5 mL-2.5 mL) was added a solution of the compound obtained in step 1 (0.51 g) in THF-diethyl ether (2.5 mL-2.5 mL), and the resulting mixture was stirred at room temperature for 2 hr under a nitrogen atmosphere. 1N Aqueous sodium hydroxide solution (0.079 mL), saturated aqueous ammonium chloride (0.079 mL) and water (0.079 mL) were added, and the resulting mixture was stirred at room temperature for 3 hr. The precipitate was removed by filtration, and the filtrate was concentrated under reduced pressure. The residue was purified by silica gel column chromatography (solvent gradient; 0→40% ethyl acetate/hexane) to give 4-benzyl-8-(3-chlorophenoxy)-2,3,4,5-tetrahydropyrido[3,2-f][1,4]oxazepine (0.25 g, 49%) as a white powder.

$^1$H-NMR (CDCl$_3$): δ3.05-3.07 (2H, m), 3.67 (2H, s), 3.70 (2H, s), 4.17-4.20 (2H, m), 6.56 (1H, d, J=7.8 Hz), 6.99-7.02 (1H, m), 7.11 (1H, s), 7.11-7.13 (1H, m), 7.24-7.34 (6H, m), 7.38 (1H, d, J=7.8 Hz)

(Step 3)

To a solution of the compound obtained in step 2 (0.23 g) in dichloroethane (3 mL) was added 1-chloroethyl chloroformate (0.074 mL), and the resulting mixture was stirred at 90° C. for 2 hr. The solvent was evaporated under reduced pressure, and methanol (3 mL) was added. The mixture was stirred at 80° C. for 1 hr. Diisopropyl ether (3 mL) was added, and the precipitate was collected by filtration, and recrystallized from ethanol-diisopropyl ether to give the title compound (0.18 g, 89%) as a white powder.

$^1$H-NMR (DMSO-d$_6$): δ3.46 (2H, brs), 4.31 (4H, brs), 6.86 (1H, d, J=8.1 Hz), 7.10-7.13 (1H, m), 7.26 (1H, s), 7.30-7.34 (1H, m), 7.44-7.49 (1H, m), 7.97 (1H, d, J=8.1 Hz), 9.77 (2H, brs)

MS (ESI+): 277 (M−HCl+H)

Example 34

8-(4-chlorophenoxy)-2,3,4,5-tetrahydropyrido[3,2-f][1,4]oxazepine hydrochloride (Step 1)

A mixture of the compound obtained in Example 28, step 1 (0.50 g), 4-chlorophenol (0.22 mL), potassium carbonate (0.76 g) and DMF (10 mL) was stirred at 100° C. for 16 hr. The reaction solution was poured into water, and the resulting product was extracted with ethyl acetate. The organic layer was washed with water and saturated brine and dried, and the solvent was evaporated under reduced pressure. The residue was purified by silica gel column chromatography (solvent gradient; 0→40% ethyl acetate/hexane) to give 4-benzyl-8-(4-chlorophenoxy)-3,4-dihydropyrido[3,2-f][1,4]oxazepin-5(2H)-one (0.59 g, 84%) as a white powder.

$^1$H-NMR (CDCl$_3$): δ3.57-3.60 (2H, m), 4.31-4.33 (2H, m), 4.80 (2H, s), 6.70 (1H, d, J=8.5 Hz), 7.10 (2H, d, J=9.0 Hz) 7.26-7.40 (7H, m), 8.61 (1H, d, J=8.5 Hz)

(Step 2)

To a mixture of lithium aluminum hydride (0.076 g) and THF-diethyl ether solution (2.5 mL-2.5 mL) was added a solution of the compound obtained in step 1 (0.51 g) in THF-diethyl ether (2.5 mL-2.5 mL), and the resulting mixture was stirred at room temperature for 2 hr under a nitrogen atmosphere. 1N Aqueous sodium hydroxide solution (0.076 mL), saturated aqueous ammonium chloride (0.076 mL) and water (0.076 mL) were added, and the resulting mixture was stirred at room temperature for 3 hr. The precipitate was removed by filtration, and the filtrate was concentrated under reduced pressure. The residue was purified by silica gel column chromatography (solvent gradient; 0→40% ethyl acetate/hexane) to give 4-benzyl-8-(4-chlorophenoxy)-2,3,4,5-tetrahydropyrido[3,2-f][1,4]oxazepine (0.20 g, 42%) as a white powder.

¹H-NMR(CDCl₃): δ3.05-3.08 (2H, m), 3.68 (2H, s), 3.70 (2H, s), 4.17-4.20 (2H, m), 6.55 (1H, d, J=8.0 Hz), 7.06 (2H, d, J=8.8 Hz), 7.26-7.36 (7H, m), 7.37 (1H, d, J=8.0 Hz)
(Step 3)
To a solution of the compound obtained in step 2 (0.19 g) in dichloroethane (3 mL) was added 1-chloroethyl chloroformate (0.062 mL), and the resulting mixture was stirred at 90° C. for 2 hr. The solvent was evaporated under reduced pressure, and methanol (3 mL) was added. The mixture was stirred at 80° C. for 1 hr. Diisopropyl ether (3 mL) was added, and the precipitate was collected by filtration, and recrystallized from ethanol-diisopropyl ether to give the title compound (0.14 g, 87%) as a white powder.
¹H-NMR (DMSO-d₆): δ3.40-3.50 (2H, m), 4.30 (4H, brs), 6.84 (1H, d, J=8.1 Hz), 7.17 (2H, d, J=8.8 Hz), 7.49 (2H, d, J=8.8 Hz), 7.95 (1H, d, J=8.1 Hz), 9.68 (2H, brs)
MS (ESI+): 277 (M−HCl+H)

Example 35

(−)-8-(1-cyclopropylethoxy)-2,3,4,5-tetrahydropyrido[3,2-f][1,4]oxazepine 0.5 succinate (Step 1)
The compound obtained in Example 15, step 1 (0.83 g) was optically resolved by chiral HPLC.
Chiral HPLC conditions
column: CHIRALCEL OJ 50 mmID×500 mL
solvent: hexane/ethanol/methanol/TFA=900/50/50/1
flow rate: 80 mL/min
temperature: 30° C.
detection method: UV220 nm
A mixture of a colorless oil (0.35 g) obtained by concentrating fractions with short retention time under reduced pressure, 20% Pd(OH)₂/C (0.040 g) and methanol (10 mL) was stirred at 50° C. for 3 hr under a hydrogen atmosphere. The insoluble material was removed by filtration, and the filtrate was concentrated under reduced pressure. The residue was purified by basic silica gel column chromatography (solvent gradient; 0→50% ethyl acetate/hexane) to give optically active 8-(1-cyclopropylethoxy)-2,3,4,5-tetrahydropyrido[3,2-f][1,4]oxazepine (0.21 g, 85%) as a colorless oil.
¹H-NMR (CDCl₃): δ0.27-0.32 (1H, m), 0.37-0.40 (1H, m), 0.50-0.54 (2H, m), 1.00-1.15 (1H, m), 1.36 (3H, d, J=6.3 Hz), 1.58 (1H, brs), 3.21-3.20 (2H, m), 3.86 (2H, s), 4.17-4.20 (2H, m), 4.55-4.70 (1H, m), 6.40 (1H, d, J=8.0 Hz), 7.36 (1H, d, J=8.0 Hz)
(Step 2)
To a solution of the compound obtained in step 1 (0.19 g) in ethanol (5 mL) was added 0.5 M succinic acid/methanol solution (0.85 mL), and the solvent was evaporated under reduced pressure. The obtained residue was recrystallized from ethyl acetate-hexane to give the title compound (0.17 g, 71%) as a white powder.
¹H-NMR (CDCl₃): δ0.27-0.33 (1H, m), 0.37-0.43 (1H, m), 0.49-0.55 (2H, m), 1.00-1.20 (1H, m), 1.36 (3H, d, J=6.2 Hz), 2.50&2.74 (total 2H, m), 2.74 (2H, brs), 3.28-3.31 (2H, m), 3.93 (2H, s), 4.21-4.24 (2H, m), 4.55-4.70 (1H, m), 6.42 (1H, d, J=8.1 Hz), 7.39 (1H, d, J=8.1 Hz)
MS (ESI+): 235 (M−0.5C₄H₆C₄O₄+H)
[α]$_D^{20}$ −18.8 (c 0.5, MeOH)

Example 36

(+)-8-(1-cyclopropylethoxy)-2,3,4,5-tetrahydropyrido[3,2-f][1,4]oxazepine 0.5 succinate (Step 1)
The compound obtained in Example 15, step 1 (0.83 g) was optically resolved by chiral HPLC
Chiral HPLC conditions
column: CHIRALCEL OJ 50 mmID×500 mL .
solvent: hexane/ethanol/methanol/TFA=900/50/50/1
flow rate: 80 mL/min
temperature: 30° C.
detection method: UV220 nm
A mixture of a colorless oil (0.37 g) obtained by concentrating fractions with long retention time under reduced pressure, 20% Pd(OH)₂/C (0.040 g) and methanol (10 mL) was stirred at 50° C. for 3 hr under a hydrogen atmosphere. The insoluble material was removed by filtration, and the filtrate was concentrated under reduced pressure. The residue was purified by basic silica gel column chromatography (solvent gradient; 0→50% ethyl acetate/hexane) to give optically active 8-(1-cyclopropylethoxy)-2,3,4,5-tetrahydropyrido[3,2-f][1,4]oxazepine (0.22 g, 85%) as a colorless oil.
¹H-NMR (CDCl₃): δ0.27-0.32 (1H, m), 0.37-0.40 (1H, m), 0.50-0.54 (2H, m), 1.00-1.15 (1H, m), 1.36 (3H, d, J=6.3 Hz), 1.58 (1H, brs), 3.21-3.24 (2H, m), 3.86 (2H, s), 4.17-4.20 (2H, m), 4.55-4.70 (1H, m), 6.40 (1H, d, J=8.0 Hz), 7.36 (1H, d, J=8.0 Hz)
(Step 2)
To a solution of the compound obtained in step 1 (0.20 g) in ethanol (5 mL) was added 0.5M succinic acid/methanol solution (0.90 and the solvent was evaporated under reduced pressure. The obtained residue was recrystallized from ethyl acetate-hexane to give the title compound (0.17 g, 67%) as a white powder.
¹H-NMR (CDCl₃): δ0.25-0.32 (1H, m), 0.38-0.45 (1H, m), 0.49-0.55 (2H, m), 1.00-1.20 (1H, m), 1.36 (3H, d, J=6.2 Hz), 2.47&4.14 (total 2H, m), 2.47 (2H, brs), 3.29 (2H, brs), 3.96 (2H, s), 4.22 (2H, brs), 4.55-4.65 (1H, m), 6.42 (1H, d, J=7.9 Hz), 7.41 (1H, d, J=7.9 Hz)
MS (ESI+): 235 (M−0.5C₄H₆C₄+H)
[α]$_D^{20}$ +18.2 (c 0.5, MeOH)

Example 37

8-(isopropylthio)-2,3,4,5-tetrahydropyrido[3,2-f][1,4]oxazepine hydrochloride (Step 1)
A mixture of the compound obtained in Example 28, step 1 (0.50 g), isopropylthiol (0.20 potassium carbonate (0.51 g) and DMF (10 mL) was stirred at room temperature for 15 hr. The reaction solution was poured into water, and the resulting product was extracted with ethyl acetate. The organic layer was washed twice with water and saturated brine and dried, and the solvent was evaporated under reduced pressure. The residue was purified by silica gel column chromatography (solvent gradient; 0→40% ethyl acetate/hexane) to give 4-benzyl-8-(isopropylthio)-3,4-dihydropyrido[3,2-f][1,4]oxazepin-5(2H)-one (0.38 g, 63%) as a white powder.
¹H-NMR (CDCl₃): δ1.40 (6H, d, J=6.9 Hz), 3.58-3.61 (2H, m), 3.98-4.07 (1H, m), 4.36-4.39 (2H, m), 4.81 (2H, s), 6.96 (1H, d, J=8.3 Hz), 7.27-7.37 (5H, m), 8.33 (1H, d, J=8.3 Hz)
(Step 2)
To a mixture of lithium aluminum hydride (0.061 g) and diethyl ether (2.0 mL) was added a solution of the compound obtained in step 1 (0.35 g) in diethyl ether (3.0 mL), and the resulting mixture was stirred at room temperature for 2 hr under a nitrogen atmosphere. 1N Aqueous sodium hydroxide solution (0.061 mL), saturated aqueous ammonium chloride (0.061 mL) and water (0.061 mL) were added, and the resulting mixture was stirred at room temperature for 3 hr. The precipitate was removed by filtration, and the filtrate was concentrated under reduced pressure. The residue was purified by silica gel column chromatography (25% ethyl acetate/hexane) to give 4-benzyl-8-(isopropylthio)-2,3,4,5-tetrahydropyrido[3,2-f][1,4]oxazepine (0.26 g, 79%) as a colorless oil.

$^1$H-NMR (CDCl$_3$): δ1.38 (6H, d, J=6.9 Hz), 3.07-3.10 (2H, m), 3.67 (2H, s), 3.68 (2H, s), 3.90-4.05 (1H, m), 4.21-4.24 (2H, m), 6.86 (1H, d, J=7.8 Hz), 7.18 (1H, d, J=7.8 Hz), 7.26-7.35 (5H, m)

(Step 3)

To a solution of the compound obtained in step 2 (0.24 g) in dichloroethane (5 mL) was added 1-chloroethyl chloroformate (0.090 mL), and the resulting mixture was stirred at 90° C. for 2 hr. The solvent was evaporated under reduced pressure, and methanol (5 mL) was added. The mixture was stirred at 80° C. for 2 hr. The solvent was evaporated under reduced pressure, the residue was crystallized from ethanol-diisopropyl ether, and the obtained solid was purified by preparative HPLC. To the obtained residue was added 4N hydrogen chloride/ethyl acetate, and the resulting mixture was recrystallized from ethanol-diisopropyl ether to give the title compound (0.11 g, 56%) as a white powder.

$^1$H-NMR (DMSO-d$_6$): δ1.33 (6H, d, J=6.8 Hz), 3.49 (2H, brs), 3.80-3.90 (1H, m), 4.25-4.40 (4H, m), 7.07 (1H, d, J=8.0 Hz). 7.73 (1H, d, J=8.0 Hz), 9.59 (2H, brs)

MS (ESI+): 225 (M−HCl+H)

LC-MS analysis in the following Example 38 to Example 62 was performed under the following conditions.

measurement device: Waters LC-MS system
HPLC part: Agilent, HP1100
MS part: Micromass, ZMD
column: CAPCELL PAK C18UG120, S-3 μm, 1.5×35 mm (Shiseido Co., Ltd.)
solvent: SOLUTION A; 0.05% trifluoroacetic acid-containing water, SOLUTION B; 0.04% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
injection volume: 2 μL, flow rate: 0.5 mL/min, detection method: UV220 nm
MS conditions ionization method: ESI In addition, purification by high polar preparative HPLC in the following Example 38 to Example 62 was performed under the following conditions.

apparatus: Gilson Inc. High Throughput purification system
column: Combiprep Hydrospher C18, 50×20 mm (YMC)
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=98/2), 1.00 min (SOLUTION A/SOLUTION B=98/2), 5.20 min (SOLUTION A/SOLUTION B=60/40), 5.40 min (SOLUTION A/SOLUTION B=5/95), 6.40 min (SOLUTION A/SOLUTION B=5/95), 6.50 min (SOLUTION A/SOLUTION B=98/2), 6.60 min (SOLUTION A/SOLUTION B=98/2)
flow rate: 20 mL/min, detection method: UV220 nm Example 38

8-cyclopentyloxy-2,3,4,5-tetrahydropyrido[3,2-f][1,4]oxazepine 2TFA salt

A solution of cyclopropanol in toluene (0.24 mol/L, 0.50 mL; 0.12 mmol) was placed in a reaction container, sodium hydride (0.008 g; 0.20 mmol) was added at room temperature, and the resulting mixture was stirred for 1 hr. A solution of tert-butyl 8-chloro-2,3-dihydropyrido[3,2-f][1,4]oxazepine-4(5H)-carboxylate (0.2 M) in toluene (0.50 mL; 0.10 mmol), BINAP (0.0022 g; 0.0036 mmol) and Pd$_2$(dba)$_3$ (0.0014 g; 0.0015 mmol) were added in this order, the reaction container was purged with argon and the resulting mixture was stirred at 100° C. for 24 hr with heating. The reaction mixture was cooled to room temperature, water (2 mL) was added, and the resulting mixture was extracted with ethyl acetate (3 mL). The ethyl acetate solvent was evaporated under reduced pressure, the residue was dissolved in DMSO (1 mL), and the solution was purified by preparative HPLC to give the title compound as an N-protected form. TFA (1.5 mL) was added to the protected form, and the resulting mixture was stirred at room temperature for 14 hr. TFA was evaporated under reduced pressure, and the residue was dissolved in water (1 mL). The solution was purified by high polar preparative HPLC to give the title compound as a TFA salt.

yield: 0.027 g
LC-MS analysis: purity 100%
MS (ESI+): 235 (M−2TFA+H)

Examples 39-62

Using the tetrahydropyridooxazepine intermediate described in Example 38 and the corresponding alcohol reagent and according to a method similar to that described in Example 38, the compounds of the following Examples 39-62 were obtained.

Example 39

N,N-dimethyl-2-(2,3,4,5-tetrahydropyrido[3,2-f][1,4]oxazepine-8-yloxy)ethaneamine 3TFA salt yield: 0.018 g
LC-MS analysis: purity 80%
MS (ESI+): 238 (M−3TFA+H)

Example 40

8-(3-methoxypropoxy)-2,3,4,5-tetrahydropyrido[3,2-f][1,4]oxazepine 2TFA salt yield: 0.037 g
LC-MS analysis: purity 99%
MS (ESI+): 239 (M−2TFA+H)

Example 41

8-(2,2,2-trifluoroethoxy)-2,3,4,5-tetrahydropyrido[3,2-f][1,4]oxazepine 2TFA salt yield: 0.023 g
LC-MS analysis: purity 99%
MS (ESI+): 249 (M−2TFA+H)

Example 42

8-(tetrahydrofuran-2-ylmethoxy)-2,3,4,5-tetrahydropyrido[3,2-f][1,4]oxazepine 2TFA salt yield: 0.026 g LC-MS analysis: purity 99%
MS (ESI+): 251 (M−2TFA+H)

Example 43

N,N-dimethyl-3-(2,3,4,5-tetrahydropyrido[3,2-f][1,4]oxazepin-8-yloxy)propan-1-amine 3TFA salt yield: 0.037 g
LC-MS analysis: purity 80%
MS (ESI+): 252 (M−2TFA+H)

Example 44

N,N-dimethyl-2-(2,3,4,5-tetrahydropyrido[3,2-f][1,4]oxazepin-8-yloxy)propan-1-amine 3TFA salt yield: 0.014 g
LC-MS analysis: purity 100%
MS (ESI+): 252 (M−3TFA+H)

Example 45

8-(2-methoxy-1-methylethoxy)-2,3,4,5-tetrahydropyrido[3,2-f][1,4]oxazepine 2TFA salt yield: 0.0068 g LC-MS analysis: purity 100%
MS (ESI+): 253 (M−2TFA+H)

Example 46

8-(pyridin-3-ylmethoxy)-2,3,4,5-tetrahydropyrido[3,2-f][1,4]oxazepine 3TFA salt yield: 0.018 g
LC-MS analysis: purity 99%
MS (ESI+): 258 (M−3TFA+H)

Example 47

8-[(1-methyl-1H-imidazol-2-yl)methoxy]-2,3,4,5-tetrahydropyrido[3,2-f][1,4]oxazepine 2TFA salt yield: 0.014 g LC-MS analysis: purity 98%
MS (ESI+): 261 (M−2TFA+H)

Example 48

8-(1,3-thiazol-2-ylmethoxy)-2,3,4,5-tetrahydropyrido[3,2-f][1,4]oxazepine 2TFA salt yield: 0.013 g LC-MS analysis: purity 99%
MS (ESI+): 264 (M−2TFA+H)

Example 49

8-(tetrahydro-2H-pyran-2-ylmethoxy)-2,3,4,5-tetrahydropyrido[3,2-f][1,4]oxazepine 2TFA salt yield: 0.016 g LC-MS analysis: purity 100%
MS (ESI+): 265 (M−2TFA+H)

Example 50

8-[(3-methylhexyl)oxy]-2,3,4,5-tetrahydropyrido[3,2-f][1,4]oxazepine 2TFA salt yield: 0.017 g LC-MS analysis: purity 100%
MS (ESI+): 265 (M−2TFA+H)

Example 51

N,N-diethyl-2-(2,3,4,5-tetrahydropyrido[3,2-f][1,4]oxazepin-8-yloxy)ethanamine 3TFA salt yield: 0.028 g
LC-MS analysis: purity 80%
MS (ESI+): 266 (M−3TFA+H)

Example 52

8-[(2-fluorobenzyl)oxy]-2,3,4,5-tetrahydropyrido[3,2-f][1,4]oxazepine 2TFA salt yield: 0.032 g
LC-MS analysis: purity 98%
MS (ESI+): 275 (M−2TFA+H)

Example 53

1-[2-(2,3,4,5-tetrahydropyrido[3,2-f][1,4]oxazepin-8-yloxy)ethyl]pyrrolidin-2-one 2TFA salt yield: 0.021 g
LC-MS analysis: purity 99%
MS (ESI+): 278 (M−2TFA+H)

Example 54

8-[3-methyl-1-(1-methylethyl)butoxy]-2,3,4,5-tetrahydropyrido[3,2-f][1,4]oxazepine 2TFA salt yield: 0.026 g LC-MS analysis: purity 100%
MS (ESI+): 279 (M−2TFA+H)

Example 55

1-[3-(2,3,4,5-tetrahydropyrido[3,2-f][1,4]oxazepin-8-yloxy)propyl]pyrrolidin-2-one 2TFA salt yield: 0.026 g LC-MS analysis: purity 99%
MS (ESI+): 292 (M−2TFA+H)

Example 56

8-(1-methyl-2-phenoxyethoxy)-2,3,4,5-tetrahydropyrido[3,2-f][1,4]oxazepine 2TFA salt yield: 0.023 g LC-MS analysis: purity 100%
MS (ESI+): 301 (M−2TFA+H)

Example 57

8-[2-(1H-indol-3-yl)ethoxy]-2,3,4,5-tetrahydropyrido[3,2-f][1,4]oxazepine 2TFA salt yield: 0.0063 g
LC-MS analysis: purity 100%
MS (ESI+): 310 (M−2TFA+H)

Example 58

2-[2-(2,3,4,5-tetrahydropyrido[3,2-f][1,4]oxazepin-8-yloxy)ethyl]-2H-1,4-benzooxazin-3(4H)-one 2TFA salt yield: 0.0052 g LC-MS analysis: purity 100%
MS (ESI+): 342 (M−2TFA+H)

Example 59

2,2-dimethyl-3-(2,3,4,5-tetrahydropyrido[3,2-f][1,4]oxazepin-8-yloxy)propane-1-sulfonamide 2TFA salt yield: 0.0022 g
LC-MS analysis: purity 97%
MS (ESI+): 316 (M−2TFA+H)

Example 60

8-[(1-methyl-1H-benzotriazol-5-yl)methoxy]-2,3,4,5-tetrahydropyrido[3,2-f][1,4]oxazepine 2TFA salt yield: 0.026 g
LC-MS analysis: purity 99%
MS (ESI+): 312 (M−2TFA+H)

Example 61

8-[(2-morpholin-4-ylbenzyl)oxy]-2,3,4,5-tetrahydropyrido[3,2-f][1,4]oxazepine 2TFA salt yield: 0.018 g
LC-MS analysis: purity 87%
MS (ESI+): 342 (M−2TFA+H)

Example 62

8-[(2-piperidin-1-ylpyridin-3-yl)methoxy]-2,3,4,5-tetrahydropyrido[3,2-f][1,4]oxazepine 2TFA salt yield: 0.015 g LC-MS analysis: purity 80%
MS (ESI+): 341 (M−2TFA+H)

The chemical structures of the Example compounds are shown in the following Table 1-Table 3.

TABLE 1

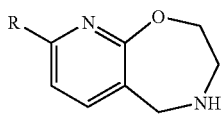

| Ex. No. | R | salt |
|---|---|---|
| 1 | (CH3)3C-O- | |
| 2 | (CH3)3C-CH2-O- | succinate |
| 3 | (CH3)2CH-CH2-O- | HCl |
| 4 | (CH3)2CH-O- | HCl |
| 5 | (CH3)2CH-O-CH2- | 0.5 succinate |
| 6 | (CH3)2CH-CH(CH3)-O- | HCl |
| 7 | cyclopropyl-CH2-O- | HCl |
| 8 | cyclobutyl-O- | HCl |
| 9 | cyclopentyl-O- | HCl |
| 10 | cyclohexyl-O- | HCl |
| 11 | 2,6-dimethylcyclohexyl-O- | HCl |
| 12 | 2-methylcyclohexyl-O- | HCl |
| 13 | CH3CH2-O-CH2- | HCl |

TABLE 1-continued

R group structure: R-pyrido-oxazepine core (pyridine fused with oxazepine ring containing NH)

| Ex. No. | R | salt |
|---------|---|------|
| 14 | (1S)-1-methyl-2-methoxycyclopentyl | 2HCl |
| 15 | 1-cyclopropyl-1-methoxyethyl | — |
| 16 | 1-cyclopropyl-1-methoxyethyl | 5.0 succonate |
| 17 | H₃C-CH₂-CH(OMe)-CH₃ (1-methoxybutyl) | HCl |
| 18 | benzyl methoxymethyl | HCl |
| 19 | H₃C-CH₂-CH₂-OCH₃ (methoxypropyl) | HCl |
| 20 | (CH₃)₃C-CH(OCH₃)-CH₃ | HCl |

TABLE 2

Same core structure.

| Ex. No. | R | salt |
|---------|---|------|
| 21 | H₃C-CH(CH₂CH₃)-CH(OCH₃)-CH₃ | HCl |
| 22 | H₃C-CH(CH₃)-CH(OCH₃) | HCl |
| 23 | 4,4-difluoro-1-methoxycyclohexyl | HCl |
| 24 | (H₃C)₂CH-CH(OCH₃)-CH₃ | HCl |
| 25 | (H₃C)₂CH-CH(OCH₃)-CH₃ (stereoisomer) | HCl |
| 26 | H₃C-CH₂-CH(OCH₃)-CH₃ | HCl |
| 27 | H₃C-CH₂-CH(OCH₃)-CH₃ (stereoisomer) | HCl |
| 28 | 2-methoxyphenyl | HCl |
| 29 | 1-cyclopentyl-1-methoxyethyl | HCl |
| 30 | 1-cyclohexyl-1-methoxyethyl | HCl |
| 31 | dicyclopropyl(methoxy)methyl | 0.5 succinate |
| 32 | 2-chloro-methoxyphenyl | HCl |
| 33 | 3-chloro-methoxyphenyl | HCl |
| 34 | 4-chloro-methoxyphenyl | HCl |

TABLE 2-continued

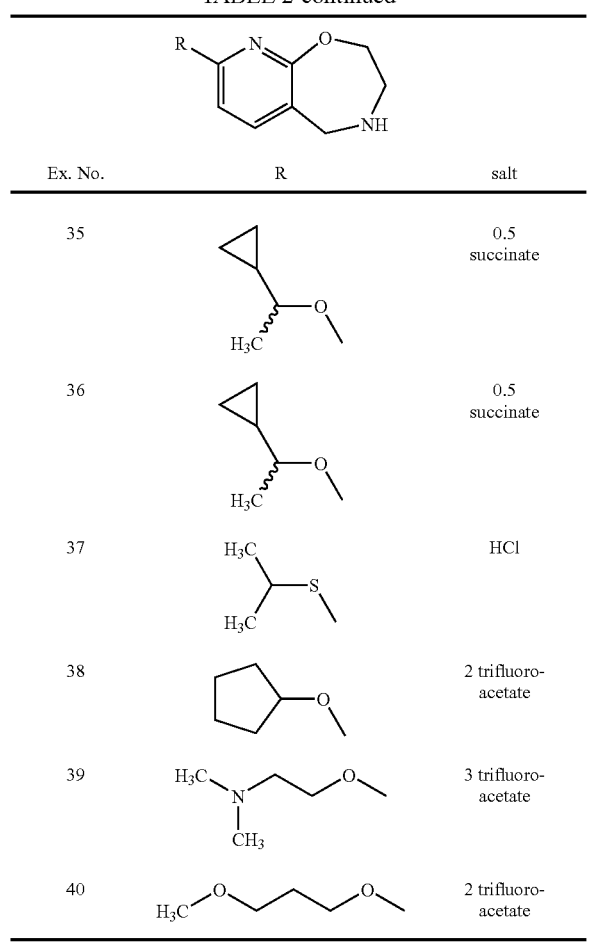

| Ex. No. | R | salt |
|---|---|---|
| 35 | (cyclopropyl-CH(OCH3)-, H3C) | 0.5 succinate |
| 36 | (cyclopropyl-CH(OCH3)-, H3C) | 0.5 succinate |
| 37 | (H3C)2CH-S-CH3 | HCl |
| 38 | (cyclopentyl-O-CH3) | 2 trifluoroacetate |
| 39 | (CH3)2N-CH2CH2-O-CH3 | 3 trifluoroacetate |
| 40 | H3C-O-CH2CH2CH2-O-CH3 | 2 trifluoroacetate |

TABLE 3

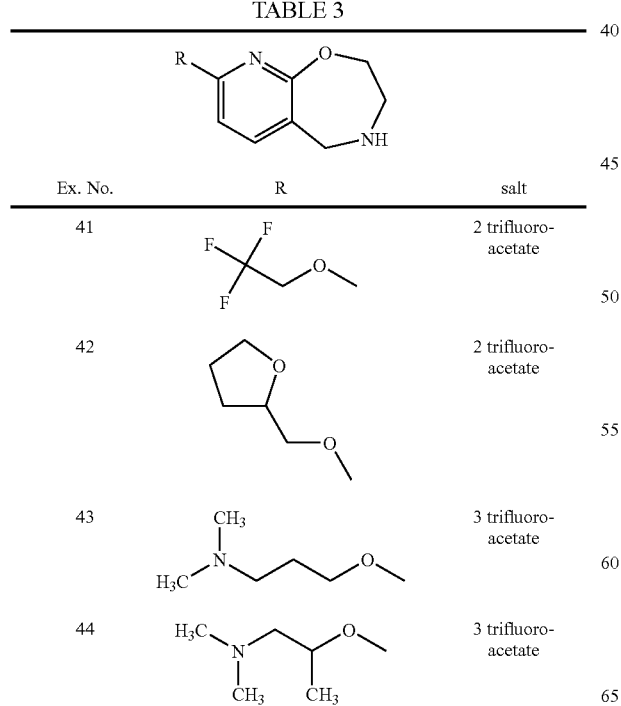

| Ex. No. | R | salt |
|---|---|---|
| 41 | CF3-CH2-O-CH3 | 2 trifluoroacetate |
| 42 | (tetrahydrofuran-2-yl)-CH2-O-CH3 | 2 trifluoroacetate |
| 43 | (CH3)2N-CH2CH2CH2-O-CH3 | 3 trifluoroacetate |
| 44 | (CH3)2N-CH2-CH(CH3)-O-CH3 | 3 trifluoroacetate |

TABLE 3-continued

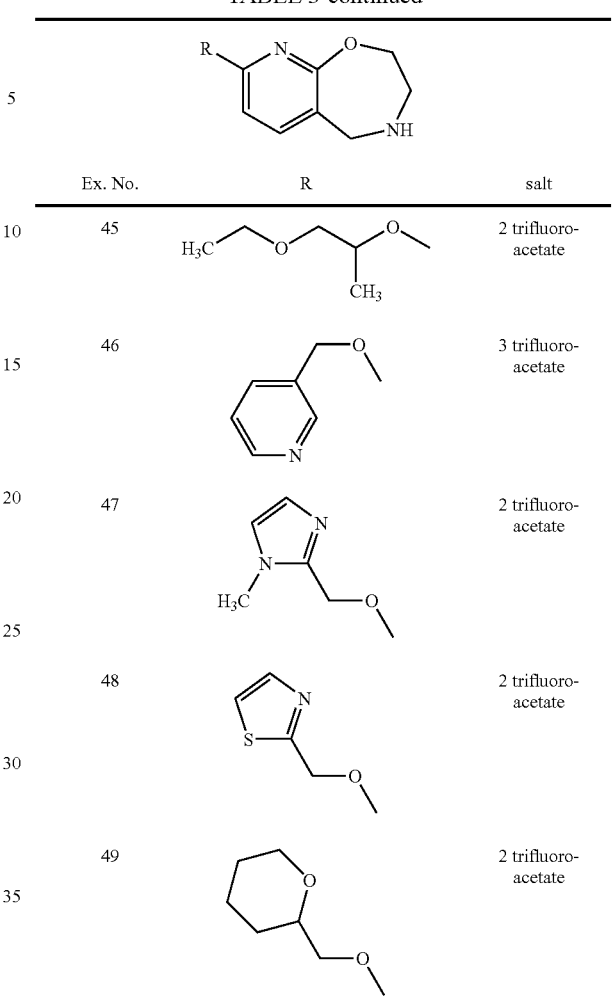

| Ex. No. | R | salt |
|---|---|---|
| 45 | H3C-CH2-O-CH2-CH(CH3)-O-CH3 | 2 trifluoroacetate |
| 46 | (pyridin-3-yl)-CH2-O-CH3 | 3 trifluoroacetate |
| 47 | (1-methylimidazol-2-yl)-CH2-O-CH3 | 2 trifluoroacetate |
| 48 | (thiazol-2-yl)-CH2-O-CH3 | 2 trifluoroacetate |
| 49 | (tetrahydropyran-2-yl)-CH2-O-CH3 | 2 trifluoroacetate |
| 50 | H3C-CH2CH2-CH(CH3)-CH2-O-CH3 | 2 trifluoroacetate |
| 51 | (H3C-CH2)2N-CH2CH2-O-CH3 | 3 trifluoroacetate |
| 52 | (2-fluorophenyl)-CH2-O-CH3 | 2 trifluoroacetate |
| 53 | (2-oxopyrrolidin-1-yl)-CH2CH2-O-CH3 | 2 trifluoroacetate |
| 54 | (H3C)2CH-CH(CH3)-CH2-CH(CH3)-O-CH3 | 2 trifluoroacetate |

TABLE 3-continued

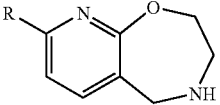

| Ex. No. | R | salt |
|---|---|---|
| 55 | 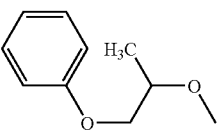 | 2 trifluoro-acetate |
| 56 | 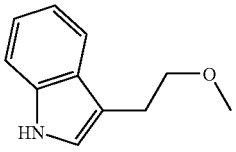 | 2 trifluoro-acetate |
| 57 | 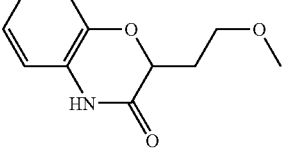 | 2 trifluoro-acetate |
| 58 | 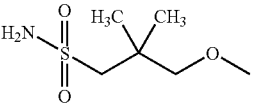 | 2 trifluoro-acetate |
| 59 | 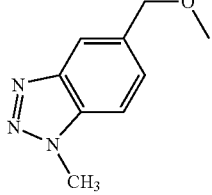 | 2 trifluoro-acetate |
| 60 | 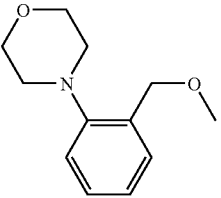 | 2 trifluoro-acetate |
| 61 | 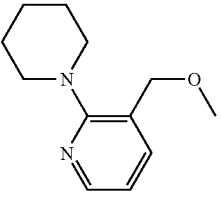 | 2 trifluoro-acetate |
| 62 |  | 3 trifluoro-acetate |

Formulation Example 1

| | | |
|---|---|---|
| (1) | The compound of Example 1 | 10 mg |
| (2) | Lactose | 60 mg |
| (3) | Cornstarch | 35 mg |
| (4) | Hydroxypropylmethylcellulose | 3 mg |
| (5) | Magnesium stearate | 2 mg |

A mixture of 10 mg of the compound obtained in Example 1, 60 mg of lactose and 35 mg of corn starch is granulated using 0.03 mL of an aqueous solution of 10 wt % hydroxypropylmethylcellulose (3 mg as hydroxypropylmethylcellulose), and then dried at 40° C. and sieved. The obtained granules are mixed with 2 mg of magnesium stearate and compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| | | |
|---|---|---|
| (1) | The compound of Example 1 | 10 mg |
| (2) | Lactose | 70 mg |
| (3) | Cornstarch | 50 mg |
| (4) | Soluble starch | 7 mg |
| (5) | Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| | | |
|---|---|---|
| (1) | Rofecoxib | 5.0 mg |
| (2) | Sodium chloride | 20.0 mg |
| (3) | Distilled water | amount to make total volume 2.0 mL |

Rofecoxib (5.0 mg) and 20.0 mg of sodium chloride are dissolved in distilled water, and water is added to make the total volume 2.0 mL. The solution is filtered, and filled into 2 mL of ampoule under sterile condition. The ampoule is sterilized, and then sealed to give a solution for injection.

Reference Formulation Example 2

| | | |
|---|---|---|
| (1) | Rofecoxib | 50 mg |
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Calcium carboxymethylcellulose | 20 mg |
| | total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin 5-HT$_{2C}$ receptor agonist activity of the Example compounds was evaluated based on the changes in the intracellular calcium concentration by the following method.

After transcription, 5-HT$_{2C}$ undergoes RNA editing of the second intracellular loop, which results in the change of three amino acids and 14 receptor isoforms. 5-HT$_{2C}$ stably expressing CHO cell that expresses VSV type of the isoform stably was purchased from Euroscreen S.A., and cultured in Ultra-CHO (BioWhittaker) medium containing 1% dialyzed bovine serum and 400 µg/mL G418. The cells were plated in a 384-well black clear bottom plate (PE Biosystems) at 5000 cells/well, cultured for 24 hr in a $CO_2$ incubator, and changes in the intracellular calcium concentration mediated by the 5-HT$_{2C}$ receptor were evaluated using Calcium Kit-Fluo 3 (Dojindo Laboratories). A calcium kit buffer containing 2.5 mM probenecid, 0.04% Pluronic F-127 and 2.5 µg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 µL. The cells were reacted at 37° C. for 1 hr to allow uptake of Fluo-3 AM into the cells and washed. The Example compound was diluted with a calcium kit buffer, and dispensed to each well of the 384-well plate (REMP) by 40 µL to give an Example compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the Example compound was added by 20 µL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The activity of the test compound is shown by the ratio relative to the maximum response by 5-HT. The results are shown in Table 4.

TABLE 4

| Example No. | ratio relative to maximum response by 5-HT (1 µM) |
|---|---|
| 1 | 98.6 |
| 3 | 100.8 |
| 5 | 97.7 |
| 13 | 97.4 |
| 16 | 98.8 |
| 23 | 83.8 |
| 24 | 94.7 |
| 25 | 98.6 |
| 26 | 97.6 |
| 27 | 99.8 |
| 28 | 91.2 |
| 35 | 93.7 |
| 36 | 104.7 |
| 37 | 94.5 |

INDUSTRIAL APPLICABILITY

Since the present compound has a superior serotonin 5-HT$_{2C}$ receptor activating action, they are useful as safe drugs for the prophylaxis or treatment of any serotonin 5-HT$_{2C}$-related diseases, for example, lower urinary tract symptom, obesity and/or organ prolapse and the like.

This application is based on a patent application No. 2007-297169 filed in Japan, the contents of which are incorporated in full herein by this reference.

The invention claimed is:
1. A compound represented by the formula

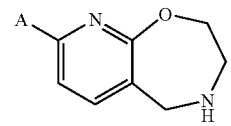

wherein
A is $-OR^1$ or $-S(O)_pR^2$;
$R^1$ and $R^2$ are the same or different and each is
(1) a hydrogen atom,
(2) a $C_{1-10}$ alkyl group optionally having substituent(s),
    a $C_{2-6}$ alkenyl group optionally having substituent(s),
    a $C_{2-6}$ alkenyl group optionally having substituent(s),
    a $C_{7-12}$ aralkyl group optionally having substituent(s),
    a $C_{6-12}$ aryl group optionally having substituent(s),
    a $C_{3-6}$ cycloalkyl group optionally having substituent(s), or
    a $C_{3-6}$ cycloalkyl-$C_{1-10}$ alkyl group optionally having substituent(s), or
(3) a 5- to 8-membered monocyclic nonaromatic heterocyclic group containing, besides carbon atoms, 1 to 4 heteroatom(s) selected from the group consisting of nitrogen atom(s), sulfur atom(s) and oxygen atom(s), optionally having substituent(s),
    a 5- to 8-membered monocyclic aromatic heterocyclic group containing, besides carbon atoms, 1 to 4 heteroatom(s) selected from the group consisting of nitrogen atom(s), sulfur atom(s) and oxygen atom(s), optionally having substituent(s),
    an 8- to 14-membered condensed nonaromatic heterocyclic group, wherein a ring corresponding to the above-mentioned 5- to 8-membered monocyclic nonaromatic heterocyclic group is condensed with a 5- or 6-membered aromatic heterocycle, a $C_{3-8}$ cycloalkane, or a $C_{6-12}$ arene, optionally having substituent(s), or an 8- to 14-membered condensed aromatic heterocyclic group, wherein a ring corresponding to the abovementioned 5- to 8-membered monocyclic aromatic heterocyclic group is condensed with a 5- or 6-membered aromatic heterocycle, a $C_{3-8}$ cycloalkane, or a $C_{6-12}$ arene, optionally having substituent(s); and p is 0, 1 or 2, or a salt thereof.

2. The compound according to claim 1, wherein $R^1$ and $R^2$ are the same or different and each is
  (1) a hydrogen atom, or
  (2) a $C_{1-10}$ alkyl group optionally having substituent(s),
    a $C_{2-6}$ alkenyl group optionally having substituent(s),
    a $C_{2-6}$ alkenyl group optionally having substituent(s),
    a $C_{7-12}$ aralkyl group optionally having substituent(s),
    a $C_{6-12}$ aryl group optionally having substituent(s),
    a $C_{3-6}$ cycloalkyl group optionally having substituent(s), or
    a $C_{3-6}$ cycloalkyl-$C_{1-10}$ alkyl group optionally having substituent(s).

3. The compound according to claim 1 or 2, wherein $R^1$ and $R^2$ are the same or different and each is
  a $C_{1-10}$ alkyl group optionally having substituent(s),
  a $C_{3-6}$ cycloalkyl group optionally having substituent(s),
  (3) a $C_{3-6}$ cycloalkyl-$C_{1-10}$ alkyl group optionally having substituent(s),
  a $C_{6-12}$ aryl group optionally having substituent(s), or
  a $C_{7-12}$ aralkyl group optionally having substituent(s).

4. The compound according to claim 1, wherein p is 0.

5. The compound according to claim 1, wherein $R^1$ is
  (1) a $C_{1-10}$ alkyl group optionally having 1 to 3 substituents selected from the group consisting of:
    (i) a halogen atom,
    (ii) a mono- or di-$C_{1-6}$ alkylamino group,
    (iii) a $C_{1-6}$ alkoxy group or a phenoxy group,
    (iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from the group consisting of:
      (a) a $C_{1-6}$ alkyl group, and
      (b) an oxo group,
    (v) a thiazolyl group, an imidazolyl group, a pyridyl group, a pyridazinyl group or an indolyl group, each optionally having 1 to 3 substituents selected from the group consisting of:
      (a) a $C_{1-6}$ alkyl group, and
      (b) a piperidinyl group, and
    (vi) a sulfamoyl group,
  (2) a $C_{7-12}$ aralkyl group optionally having 1 to 3 substituents selected from the group consisting of:
    (a) a halogen atom, and
    (b) a morpholinyl group,
  (3) a phenyl group optionally having 1 to 3 halogen atoms,
  (4) a $C_{3-6}$ cycloalkyl group optionally having 1 to 3 substituents selected from the group consisting of:
    (a) a halogen atom, and
    (b) a $C_{1-6}$ alkyl group,
  (5) a $C_{3-6}$ cycloalkyl-$C_{1-6}$ alkyl group, or
  (6) a di-$C_{3-6}$ cycloalkyl-$C_{1-6}$ alkyl group;
$R^2$ is a $C_{1-6}$ alkyl group; and
p is 0.

6. The compound according to claim 1, wherein $R^1$ is
  (1) a $C_{1-10}$ alkyl group optionally having 1 to 3 substituents selected from the group consisting of:
    (i) a halogen atom,
    (ii) a dimethylamino group or a diethylamino group,
    (iii) a methoxy group, an ethoxy group or a phenoxy group,
    (iv) a pyrrolidinyl group, a tetrahydrofuryl group, a tetrahydropyranyl group, a benzotriazolyl group or a 3,4-dihydro-2H-benzo[1,4]oxazinyl group, each optionally having 1 to 3 substituents selected from the group consisting of:
      (a) a methyl group, and
      (b) an oxo group,
    (v) a thiazolyl group, an imidazolyl group, a pyridyl group, a pyridazinyl group or an indolyl group, each optionally having 1 to 3 substituents selected from the group consisting of:
      (a) a methyl group, and
      (b) a piperidinyl group, and
    (vi) a sulfamoyl group,
  (2) a benzyl group optionally having 1 to 3 substituents selected from the group consisting of:
    (a) a halogen atom, and
    (b) a morpholinyl group,
  (3) a phenyl group optionally having 1 to 3 halogen atoms,
  (4) a $C_{3-6}$ cycloalkyl group optionally having 1 to 3 substituents selected from the group consisting of:
    (a) a halogen atom, and
    (b) a methyl group,
  (5) a $C_{3-6}$ cycloalkyl-$C_{1-2}$ alkyl group, or
  (6) a di-$C_{3-6}$ cycloalkyl-$C_{1-2}$ alkyl group;
$R^2$ is isopropyl; and
p is 0.

7. 8-Isopropoxy-2,3,4,5-tetrahydropyrido[3,2-f][1,4]oxazepine or a salt thereof.

8. (−)-8-(1-Cyclopropylethoxy)-2,3,4,5-tetrahydropyrido[3,2-f][1,4]oxazepine or a salt thereof.

9. 8-(2-Chlorophenoxy)-2,3,4,5-tetrahydropyrido[3,2-f][1,4]oxazepine or a salt thereof.

10. 8-{[(1R)-1-Methylpropyl]oxy}-2,3,4,5-tetrahydropyrido[3,2-f][1,4]oxazepine or a salt thereof.

11. 8-(Cyclobutyloxy)-2,3,4,5-tetrahydropyrido[3,2-f][1,4]oxazepine or a salt thereof.

12. 8-(Isopropylthio)-2,3,4,5-tetrahydropyrido[3,2-f][1,4]oxazepine or a salt thereof.

13. A pharmaceutical composition comprising the compound according to claim 1 or a salt thereof and a pharmaceutically acceptable carrier.

14. A method for the treatment of a lower urinary tract symptom, obesity and/or organ prolapse, comprising administering, to a mammal, an effective amount of a compound represented by the formula

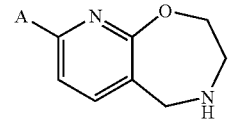

wherein
A is —$OR^1$ or —$S(O)_pR^2$;
$R^1$ and $R^2$ are the same or different and each is
  (1) a hydrogen atom,
  (2) a $C_{1-10}$ alkyl group optionally having substituent(s),
    a $C_{2-6}$ alkenyl group optionally having substituent(s),
    a $C_{2-6}$ alkenyl group optionally having substituent(s),
    a $C_{7-12}$ aralkyl group optionally having substituent(s),
    a $C_{6-12}$ aryl group optionally having substituent(s),
    a $C_{3-6}$ cycloalkyl group optionally having substituent(s), or a C$_{3-6}$ cycloalkyl-C$_{1-10}$ alkyl group optionally having substituent(s), or (3) a 5- to 8-membered monocyclic nonaromatic heterocyclic group containing, besides carbon atoms, 1 to 4 heteroatom(s) selected from the group consisting of nitrogen atom(s), sulfur atom(s) and oxygen atom(s), optionally having substituent(s), a 5- to 8-membered monocyclic aromatic heterocyclic group containing, besides carbon atoms, 1 to 4 heteroatom(s) selected from the group consisting of nitrogen atom(s), sulfur atom(s) and oxygen atom(s), optionally having substituent(s), an 8- to 14-membered condensed nonaromatic heterocyclic group, wherein a ring corresponding to the above-mentioned 5- to 8-membered monocyclic nonaromatic heterocyclic group is condensed with a 5- or 6-membered aromatic heterocycle, a C$_{3-8}$ cycloalkane, or a C$_{6-12}$ arene, optionally having substituent(s), or an 8- to 14-membered condensed aromatic heterocyclic group, wherein a ring corresponding to the above-mentioned 5- to 8-membered monocyclic aromatic heterocyclic group is condensed with a 5- or 6-membered aromatic heterocycle, a C$_{3-8}$ cycloalkane, or a C$_{6-12}$ arene, optionally having substituent(s); and p is 0, 1 or 2, or a salt thereof.

* * * * *

UNITED STATES PATENT AND TRADEMARK OFFICE
CERTIFICATE OF CORRECTION

PATENT NO. : 8,329,687 B2
APPLICATION NO. : 12/742837
DATED : December 11, 2012
INVENTOR(S) : Takahiro Matsumoto Page 1 of 1

It is certified that error appears in the above-identified patent and that said Letters Patent is hereby corrected as shown below:

In the Claims:

Claim 1, in column 78, line 44:

"a $C_{2-6}$ alkenyl group optionally having substituent(s),", should read

--a $C_{2-6}$ ~~alkenyl~~ alkynyl group optionally having substituent(s),--.

Claim 2, in column 79, line 14:

"a $C_{2-6}$ alkenyl group optionally having substituent(s),", should read

--a $C_{2-6}$ ~~alkenyl~~ alkynyl group optionally having substituent(s),--.

Claim 14, in column 80, line 63:

"a $C_{2-6}$ alkenyl group optionally having substituent(s),", should read

--a $C_{2-6}$ ~~alkenyl~~ alkynyl group optionally having substituent(s),--.

Signed and Sealed this
Seventh Day of May, 2013

Teresa Stanek Rea
*Acting Director of the United States Patent and Trademark Office*